(12) United States Patent
Lalley

(10) Patent No.: US 6,706,704 B2
(45) Date of Patent: Mar. 16, 2004

(54) METHOD OF INDUCING OPIOID ANALGESIA AND ANESTHESIA WITHOUT RESPIRATORY SUPPRESSION

(75) Inventor: Peter M. Lalley, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 10/007,596

(22) Filed: Nov. 9, 2001

(65) Prior Publication Data

US 2003/0092701 A1 May 15, 2003

(51) Int. Cl.$^7$ ...................... A61K 31/55; A61K 31/437; A61K 31/4375; A61K 31/4743
(52) U.S. Cl. ...................... 514/213; 514/280; 514/284; 514/285
(58) Field of Search ................................ 514/213, 280, 514/284, 285

(56) References Cited

PUBLICATIONS

Ballanyi et al., J. Physiology, 504(1), 127–134 (1997).*
Foote et al., Life Sciences, 42(2), 137–52 (1988).*
Bidaut–Russell et al., J. Neurochem., 57(5), 1769–73 (1991).*
Balis, G.U. and Monroe, R.R., (1964). The pharmacology of choralose, *Psychopharmacology*, 6:1–30.
Bennett, J.A., Abrams, J.T., Van Riper, D.F. and Horrow, J.C. (1997). Difficult or impossible ventilation after sufenanil–induced anesthesia is caused primarily by vocal cord disclosure, *Anesthsiol.*, 87:1070–1074.
Bianchi et al., (1995). Central control of breathing in mammals: Neuronal circuitry, membrane properties, and neurotransmitters, *Physiol. Rev.* 75:1–45.
Cohen, M, (1979) Neurogenesis of respiratory rhythm, *Physiol. Rev.*, 59:1105–1172.
Denavit–Saubie', M., Champagnat, J. and Zieglgansberger, W. (1978). Effects of opiates and methionine–enkephalin on pontine and bulbar respiratory neurones of the cat., *Brain Research*, 155:55–67.
Duffin, J., Tian, G.–F., and Peever, J.H. (2000). Functional synaptic connections among respiratory neurons, *Respiration Physiol.*, 122:237–246.
Ezure, K., (1990). Synaptic connections between medullary respiratory neurons and considerations on the genesiss of respiratory rhythm, *Progress in Neurobiology*, 35:429–450.
Fone, K.F.C. and Wilson, H., (1986). The effects of alfentanil and selected marcotic nalgesics on the rate of action potential discharge of medullary respiratory neurones in anaesthetized rats, *Br. J. Pharmacol.*, 89:67–76.
Howard and Sears, (1990), the Effects of Opiates on the Respiratory Activity of Thoracic Motoneurons in the Anaesthesized and Decerebrate Rabbit, *Journal of Physiology*, 437:181–199.

Jaffe, J.H. and Martin, W.R., (1980). Opioid analgesics and antagonists: *In: Goodman and Gilman's The Pharmacological Basis of Therapeutics*, Sixth Edition, pp. 494–534. A.G. Gilman, L.S. Goodman, A. Gilman, S.E. Mayer and K.L. Melmon (Eds.). New York, Macmillan Publishing Co., Inc.

Jaffe, J.H. and Martin, W.R., (1990). Opioid agonists and antagonists: *In: Goodman and Gilman's The Pharmacological Basis of Therapeutics*, Eighth Edition, pp. 485–521. A.G. Gilman, T.W. Rall, A.S. Nies and P. Taylor (Eds.). New York, Pergamon Press.

Johnson, S.M., Smith, J.C. and Feldman, J.L., (1996). Modulation of G i/o protein–mediated mechanisms, *Journal of Applied Physiology*, 80:2120–2133.

Killam, E.K. (1962), Drug Action on the brainstem reticular formation, *Pharmacological Reviews*, pp. 175–223.

Killam, E.K. (1968). Pharmacology of the reticular formation, *In: Psychopharmacology*. A review of progress, 1957–1967. (Ed., D.H. Efron.), Public Health Service Publication No. 1836, 41–445. pp. 411–445. Washington D.C., US Government Printing Office.

Kishioka, S., Ko, M.C., and Woods, J.H., (2000). Diltiazem enhances the analgesic but not the respiratory depressant effects of morphine in rhesus monkeys, *EUR. J. Pharmacol.*, 397:85–92.

Kreuter, F., Richter, D.W., Camerer, H. and Senekowitsch, R., (1977). Morphological and electrical description of medullary respiratory neurons of the cat, *Pfluegers Arch.*, 372:7–16.

Lalley, P.M., Bischoff, A.M., Pierrefiche, O. and Richter, D.W., (1997). cAMP–dependent protein kinase modulates excitability of medullary expiratory neurones in the cat, *Journal of Neurophysiology*, 77:1119–1131.

Laubie et al., (1986). Discharge patterns of bulbar respiratory neurones in response to the morphinomimetic agent, fentanyl, in chloralosed dogs, *Eur. J. Pharmacol.*, 122:301–309.

Long, S. and Duffin, J., (1986). The neuroneal determinants of respiratory rhythm, *Prog. Neurobiol.*, 27:101–182.

Marty, J. and Desmonts, J.M., (1981). Effects of fentanyl on respiratory pressure–volume relationship in supine anesthetized children, *Acta Anaesth. Scand.*, 25:293–296.

(List continued on next page.)

Primary Examiner—Phyllis G. Spivack
(74) Attorney, Agent, or Firm—Joseph T. Leone, Esq.; DeWitt Ross & Stevens S.C.

(57) ABSTRACT

The invention is directed to a pharmaceutical composition and a corresponding method for inhibiting respiratory depression in a mammalian subject during treatment with opiates. The composition contains in combination, an opiate or opioid analgesic or anesthetic and a $D_1$-dopamine receptor agonist in an amount sufficient to inhibit respiratory depression caused by the opiate or opioid.

23 Claims, 24 Drawing Sheets

OTHER PUBLICATIONS

Neidhart, P., Burgener, M.C. and Suter, P.M., (1989). Chest wall rigidity during fentanyl–and midazolam–fentantyl induction: ventilatory and haemodynamic effects, *Acta Anaesth. Scand.*, 33:1–5.

North, Williams, Surprenant and Christie, 1987, PNAS.

Richter, D.W., Ballantyne, D. and Remmers, J.E. (1986). How is the respiratory rhythm generated? A model, *News In Physiological Sciences*, 1:109–112.

Richter, D.W. (1996). Neural regulation of respiration: rhythmogenesis and afferent control. *In: Comprehensive human physiology*. vol. 2, R. Gregor and U. Windhorst (Eds.), Springer–Verlag, Heidelberg, 2079–2095.

Shemano, I., Wendel, H. and Ross, S.D., (1961). A pharmacological comparison of phenazocine hydrobromide and morphine sulfate as carcotic analgesics, *J. Pharmacol. Exp. Ther.*, 132:258–263.

Shook, J.E., Watkins, W.D. and Camporesi, E.M. (1990). Differential roles of opioid receptors in respiration, respiratory disease and opiate–induced respiratory depression, *American Review of Respiratory Diseases*, 33:1–16.

Travagli, R.A., Wessendorf, M. and Williams, J.T., (1996). Dendritic arbor of locus coeruleus neurones contributes to opioid inhibition. *J. Neurophysiol.*, 75:2029–2035.

Trouth, C.O., Millis, R.M., Bernard, D.G., Pan, Y., Whittaker, J.A. and Archer, P.W. (1993). Cholinergic–opioid interactions at brain stem respiratory chemosensitive areas in cats, *Neurotoxicology*, 14:459–467.

Winters, W.D., (1968). Neurophysiological studies utilizing evoked responses techniques in animals. A review of progress, 1957–1967. (Ed., D.H. Efron.), Public Health Service Publication No. 1836, 41–445, pp. 453–477, Washington D.C., US Government Printing Office.

Xie and Lewis, (1997). Involvement of cAMP–dependent protein kinase in muopioid modulation of NMDA–mediated synaptic currents, *J. Neurophysiol.*, 78:759–66.

Yeadon, M. and Kitchen, I., (1989), Opioids and respiration. *Progress in Neurobiology*, 33:1–16.

\* cited by examiner

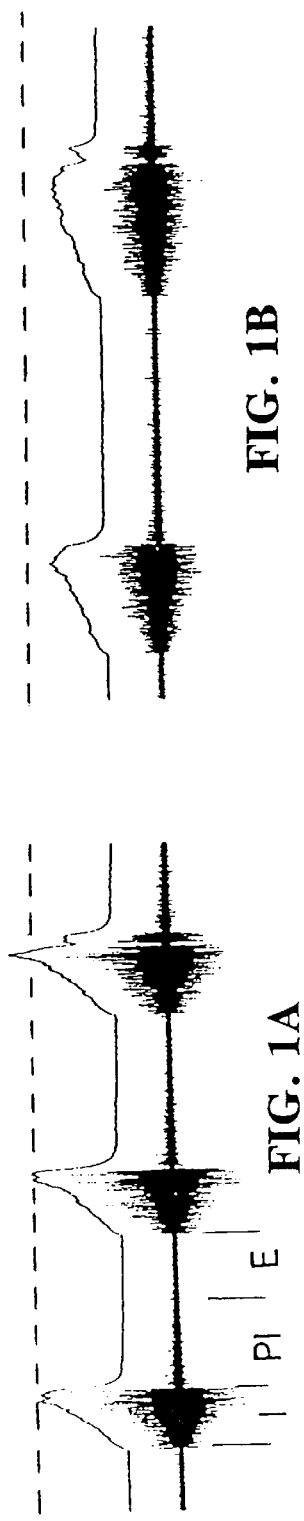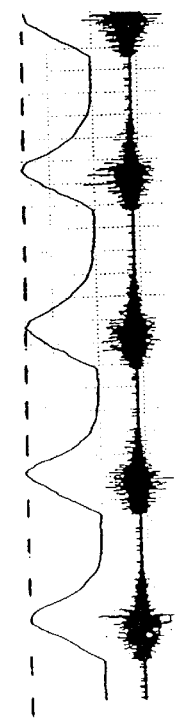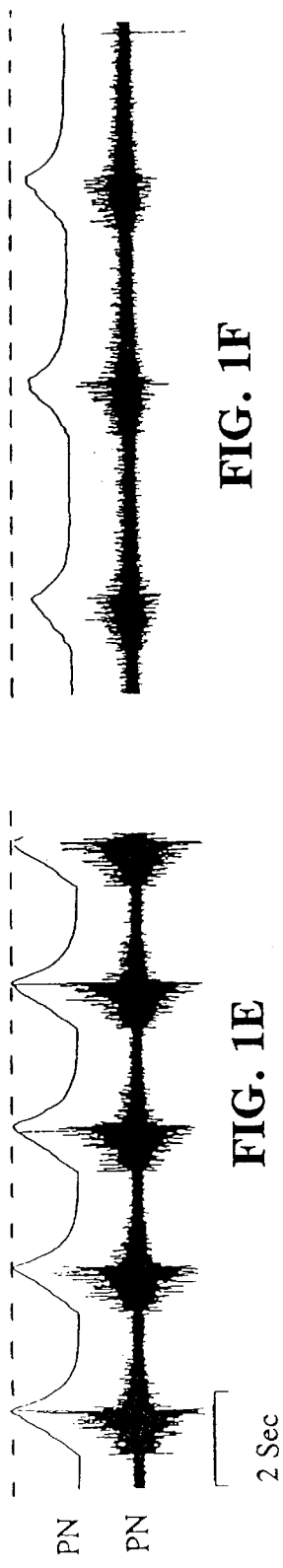
Pentobarbital Anesthesia — FIG. 1A, FIG. 1B
Chloralose Anesthesia — FIG. 1C, FIG. 1D
Midcollicular Decerebration — FIG. 1E, FIG. 1F

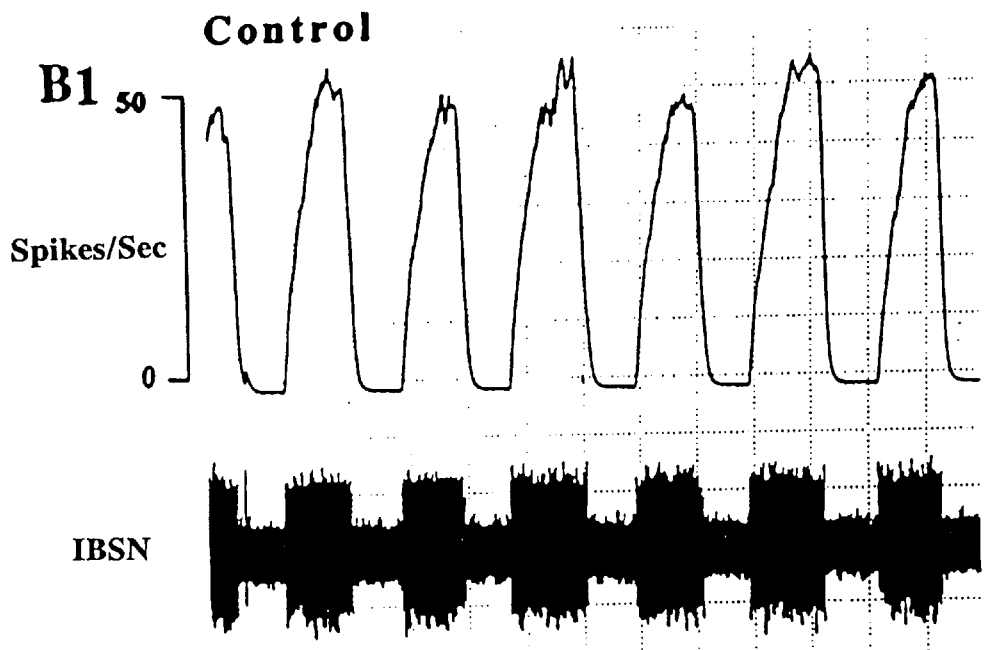
FIG. 3B(i)
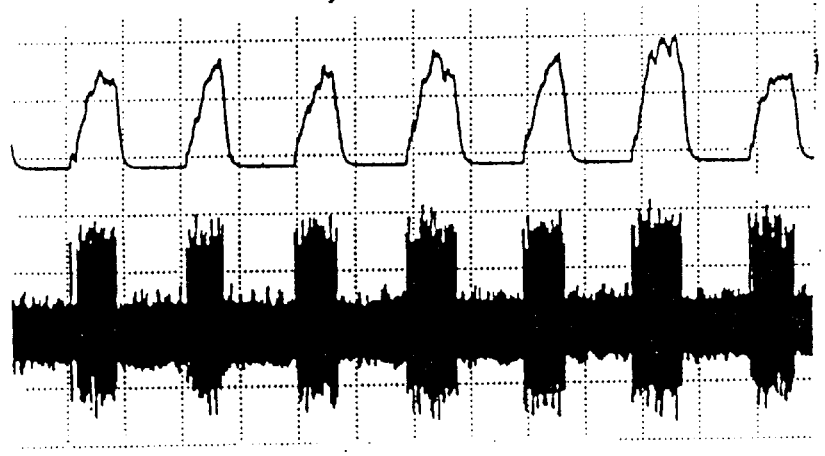
FIG. 3B(ii)

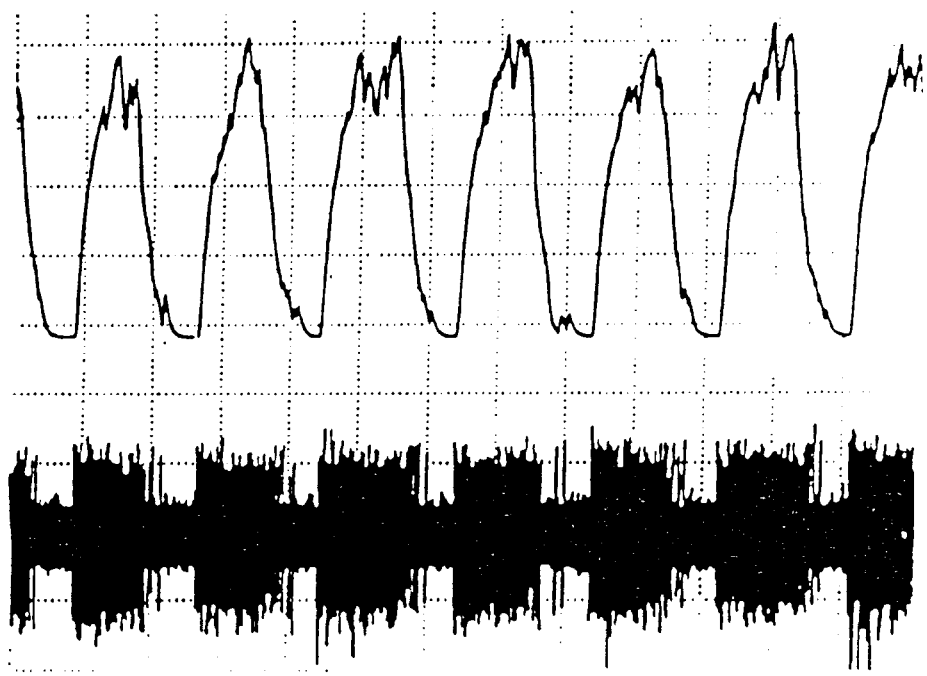
FIG. 3B(iii)

C1
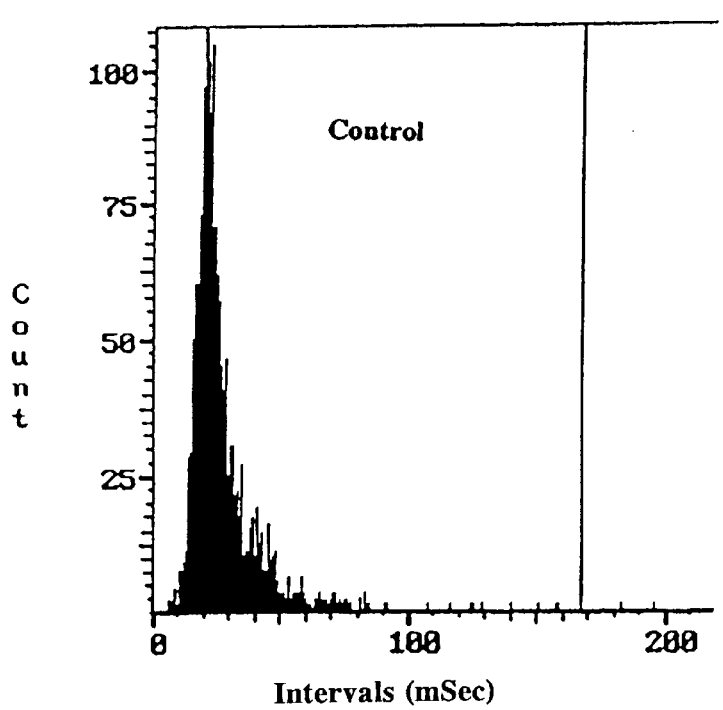
FIG. 3C(i)
C2
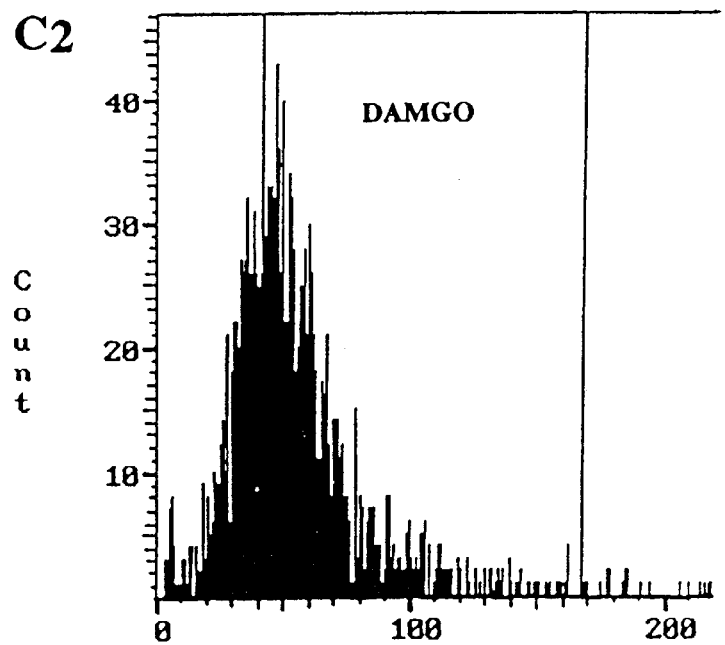
FIG. 3C(ii)

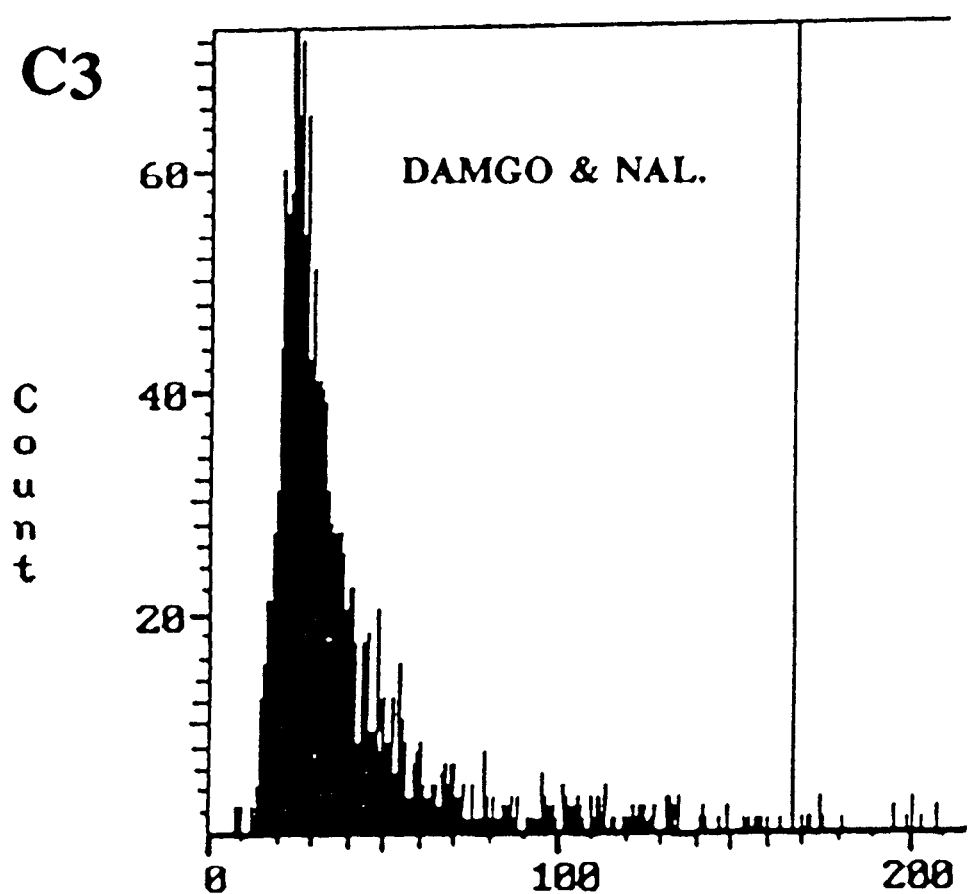
FIG. 3C(iii)

A1 Control

SEVC

HP -70 mV

A2 Fentanyl, 100 µg/kg

ETCO2 32 Torr

A3 ETCO2 52 Torr

B1

SECC

B2

B3

A  Control

B  Fentanyl 30 µg/Kg

C

Central Apnea

1 Sec

D  (±) APB , 3 mg/Kg

A  Control

B  Fentanyl 15 μg/Kg

C  APB, 1 mg/Kg

D Control

E Fentanyl
SCH 23390 100 µg/kg
(±) APB 3 mg/kg

F Doxapram 1 mg/kg

METHOD OF INDUCING OPIOID ANALGESIA AND ANESTHESIA WITHOUT RESPIRATORY SUPPRESSION

This invention was made with United States government support awarded under NIH HL65526. The United States has certain rights in this invention.

FIELD OF THE INVENTION

The invention is directed to method of inducing opioid analgesia and anesthesia in mammals, including humans, without suppressing respiration.

BACKGROUND

Opiates have long been known to disrupt respiratory rhythm and to depress breathing and respiratory sensitivity to $CO_2$ (Jaffe and Martin, 1990). The pons and medulla are known to be the primary sites where opiate drugs produce these respiratory effects (Id.). Endogenous opioids as well as $\mu$- and $\delta$-subtypes of opioid receptors are present in essentially all respiratory regions of the pons and medulla (Yeadon and Kitchen, 1989). In vivo and in vitro investigations have shown that exogenous opioids depress inspiratory and expiratory neuronal activity postsynaptically (Denavit-Saubie', Champagnat and Zieglgansberger, 1978), as well as presynaptically (Johnson, Smith and Feldman, 1996). The underlying cellular mechanisms responsible for the opiate effects on respiration have not, however, been elucidated.

Opiates are widely used medicinal agents. However, because they depress breathing, their use is contraindicated in many instances, especially in patients with compromised cardiovasculare and pulmonary function. Thus, there has been a long-felt need to harness the analgesic power of the opiates, without depressing the respiratory function of the patient.

SUMMARY OF THE INVENTION

In the present invention, actions of opiates were analyzed on bulbospinal inspiratory and expiratory neurons and on non-bulbospinal postinspiratory neurons of the medulla in cats that were either anesthetized with pentobarbital or $\alpha$-chloralose, or rendered comatose in the unanesthetized state by midcollicular decerebration. The cat respiratory network is similar to that of man. The different cat preparations were used to determine how opiate-induced respiratory responses are affected by anesthetics with different effects on the reticular activating system (RAS; Killlam, 1967). The RAS provides a source of excitatory synaptic input to the brainstem respiratory network (Richter, Ballantyne and Remmers 1986), and is also a site of action for opiates (Killam, E. K. 1963). Most of the respiratory neurons in this study were identified as bulbospinal and therefore might be directly responsible for opiate-mediated depression of tidal volume (Jaffe and Martin, 1990; Shook et al., 1990) and decreased chest wall compliance (Marty and Desmonts, 1981; Bennett, Abrams, Van Riper and Horrow, 1997; Neidhart, Burgener and Suter, 1989).

With respect to this invention, it was also important to ascertain whether anesthesia would compromise the potential of $D_1$ dopamine agonists to antagonize opioid-mediated respiratory depression. This is an important issue because opioids and anesthetics are frequently used in combination during surgical procedures.

Another objective of this work was to determine if opioid depression of the respiratory network is reversed by administration of selective $D_1$-dopamine receptor agonists. Reversal of opioid depression with a $D_1$ agonist had been previously demonstrated by Lalley and coworkers in an in vitro brainstem-spinal cord preparation of the neonatal rat (Ballanyi, Lalley, Hoch and Richter 1997). This work, however, cannot be extrapolated to in vivo efficacy due to the rudimentary nature of the in vitro spinal cord preparation. Experimentation in a more developmentally mature and intact animal model was required to determine if this type of antagonism is also possible in vivo in the respiratory network of mature mammals. The results discussed herein reveal that $D_1$ agonists are indeed effective in each of the different cat animal models, and reinstate a normal respiratory rhythm without directly stimulating the network or increasing brain stem or carotid body chemoreceptor sensitivity.

Thus, a first embodiment of the present invention is directed to a pharmaceutical composition for inducing analgesia or anasthesia in a mammalian subject, while simultaneously eliminating or inhibiting respiratory depression in the subject. The pharmaceutical composition comprises, in combination, an opiate or opioid analgesic or anesthetic, a $D_1$-dopamine receptor agonist, and a pharmaceutically-suitable carrier therefor. More specifically, in the preferred composition, the opiate or opioid is selected from the group consisting of alfentanil, buprenorphine, carfentanil, codeine, dihydrocodeine, diprenorphine, etorphine, fentanyl, heroin, hydrocodone, hydromorphone, LAAM, levorphanol, meperidine, methadone, morphine, naloxone, naltrexone, beta-hydroxy-3-methylfentanyl, oxycodone, oxymorphone, propoxyphene, remifentanil, sufentanil, tilidine, tramadol, enriched or pure enantiomers or diastereomers thereof; racemic mixtures thereof; and pharmaceutically-suitable salts thereof; and the $D_1$-dopamine receptor agonist is selected from the group consisting of ($\pm$)-1-phenyl-2,3,4,5-tetrahydro-(1H)-3-benzazepine-7,8-diol; (−)-(6aR,12bR)-4,6,6a,7,8,12b-hexahydro-7-methylindolo{4,3-a}phenanthridine; ($\pm$)-trans-10,11-dihydroxy-5,6,6a,7,8,12b-hexahydrobenzo-{a}phenanthridine; ($\pm$)-6-chloro-7,8-dihydroxy-3-allyl-1-phenyl-2,3,4,5-tetrahydro-1H-3-benzazepine; ($\pm$)-6-chloro-7, 8-dihydroxy-1-phenyl-2,3,4,5-tetrahydro-1H-3-benzazepine; ABT 431; enriched or pure enantiomers or diastereomers thereof; racemic mixtures thereof; and pharmaceutically-suitable salts thereof.

A second embodiment of the invention is directed to a method of inhibiting respiratory depression in mammals during treatment with opiates or opioids. The method comprises administering to a mammalian subject being treated with opiates or opioids, an amount of a $D_1$-dopamine receptor agonist, the amount being sufficient to inhibit respiratory depression. The preferred $D_1$-dopamine receptor agonists for use in the method are the same as those listed in the previous paragraph. Likewise, the method will function with equal success regardless of the specific opiate or opioid that is being used to treat the subject.

BRIEF DESCRIPTION OF THE FIGURES

FIGS. 1A through 1F illustrate typical disturbances of respiratory rhythm caused by administering fentanyl intravenously in cats anesthetized with either pentobarbital (FIG. 1A=control, FIG. 1B=after administration of fentanyl); $\alpha$-chloralose (FIG. 1C=control, FIG. 1D=after administration of fentanyl); or in unanesthetized decerebrate cats (FIG. 1E=control, FIG. 1F=after administration of fentanyl). Records in each panel show raw phrenic nerve activity (PN) and the moving average of phrenic nerve action potential frequency activity ($\int$PN), time constant 100 mSec. Symbols I, PI, and E in FIG. 1A denote the inspiratory, postinspiratory and expiratory phases of PN. Doses of fentanyl were 10 µg/kg in the pentobarbital- and α-chloralose-anesthetized cats, 12.5 µg/kg in the decerebrate cat.

FIGS. 3A, 3B(i), 3B(ii), 3B(iii), 3C(i), 3C(ii) and 3C(iii) are a series of traces showing depression of excitability in an inspiratory bulbospinal neuron during iontophoresis of DAMGO, a µ-selective opioid receptor agonist. FIG. 3A: Pentobarbital-anesthetized cat. The upper trace shows extracellularly-recorded discharges of an inspiratory bulbospinal neuron in the ventral respiratory group of the medulla, raw phrenic nerve activity (PNA) and the moving average of phrenic nerve action potential frequency (ISBN). FIGS. 3B(i), 3B(ii), 3B(iii): Inspiratory bulbospinal neuron discharges and their integrals under control conditions (FIG. 3B(i)), during iontophoresis of DAMGO, 50 nA from a 10 mM solution (FIG. 3B(ii)) and during simultaneous iontophoresis of DAMGO, 50 nA and Naloxonazine (25 nA, 10 mM), a µ-selective opioid receptor blocker (FIG. 3B(iii)). FIGS. 3C(i), 3C(ii), 3C(iii): Interspike interval (ISI) histograms of inspiratory bulbospinal neuron discharges. Under control conditions (FIG. 3C(i)), during iontophoresis of DAMGO (FIG. 3C(ii)) and during simultaneous iontophoresis of DAMGO and Naloxonazine (FIG. 3C(iii)).

FIGS. 4A and 4B show the effects of 7.5 µg/kg fentanyl on membrane potential of an Aug-E neuron and on phrenic nerve activity, respectively, in a chloralose-anesthetized cat. Fentanyl reduced the rate of membrane depolarization to threshold and reduced the number of action potentials to five, while slightly prolonging PNA discharges and reducing firing frequency by 200 action potentials per second. FIGS. 4C and 4D (taken from the same animal as in FIGS. 4A and 4B) show the effects of increasing the dose of fentanyl to 15 µg/kg. Increasing the dose of fentanyl further depressed rate and degree of membrane potential depolarization, abolished action potentials, and greatly prolonged the expiratory phase. PNA was severely depressed. Input resistance, calculated from the amplitude of potentials evoked by 100 pA, 80 mSec, hyperpolarizing constant current pulses, was 10 MΩ under control conditions (FIG. 4C) and after giving fentanyl (FIG. 4D).

FIGS. 6A, 6B, and 6C show membrane currents (pA) in a non-discharging E neuron recorded during single electrode voltage clamp {SEVC, holding potential (HP) −70 mV, 30 KHz switching frequency, 25% duty cycle}. FIGS. 6D, 6E, and 6F show membrane potential (mV) when recording was switched to current clamp (SECC). Records of phrenic nerve activity (PN) and the moving average of phrenic nerve action potential frequency ($PN_A$) are also shown in each figure. Dashed lines denote control levels of inspiratory phase outward current and membrane potential hyperpolarization. Controls are shown in FIGS. 6A and 6D. After administering fentanyl (100 µg/kg i.v.) (FIGS. 6B and 6E), the respiratory rhythm was abolished. Membrane potential was hyperpolarized and an increase in outward current occurred. EPSP and EPSC frequency was reduced but amplitude did not change appreciably. Hypercapnea produced by ventilation with a mixture of 5% $CO_2$, 95% $O_2$ and room air shifted membrane potential and current back toward control levels, but was insufficient to restore the respiratory rhythm (FIGS. 6C and 6F).

FIG. 7A (control) shows current clamp records of membrane potential (mV) and extracellular records of phrenic nerve activity (PN) and the moving average of phrenic nerve discharge frequency (∫PN); FIG. 7B shows the same tracings after administering fentanyl (20 µg/kg). The dose of fentanyl (20 µg/kg i.v.) was just sufficient to abolish PN and the neuron's respiratory rhythm. FIG. 7C shows the same tracings after administering doxapram (1 mg/kg). FIG. 7D (control) shows voltage clamp records of membrane currents (nA) recorded at a holding potential of −70 mV, PN and ∫PN; FIG. 7E shows the same tracings after administering fentanyl (20 µg/kg); FIG. 7F shows the same tracings after administering doxapram (1 mg/kg). Dashed lines denote membrane potential and current recorded under control conditions.

FIG. 8A is the control. FIGS. 8B and 8C show that fentanyl produces a more rapid development of inhibition in the PI neuron than in PNA. (±)-Chloro-APB restored rhythmic discharges, FIG. 8D, however reversal was not complete. Larger doses of (±)-chloro-APB (data not shown) had no further effects.

FIGS. 9A (control), 9B (fentanyl-induced apnea), and 9C (fentanyl-induced apnea treated with a $D_1$ dopamine receptor agonist) show reversal of fentanyl-induced apnea by (±)-chloro-APB. FIGS. 9D (control) and 9E (after administration of the $D_1$-dopamine receptor blocker R (+)-SCH 23390 and (±)-chloro-APB) show that PNA was not restored by (±)-chloro-APB. FIG. 9F shows that subsequent i.v. administration of the carotid body chemoreceptor stimulant doxapram reinstated phrenic nerve discharges.

DETAILED DESCRIPTION OF THE INVENTION

Abbreviations and Definitions

Figure 2:
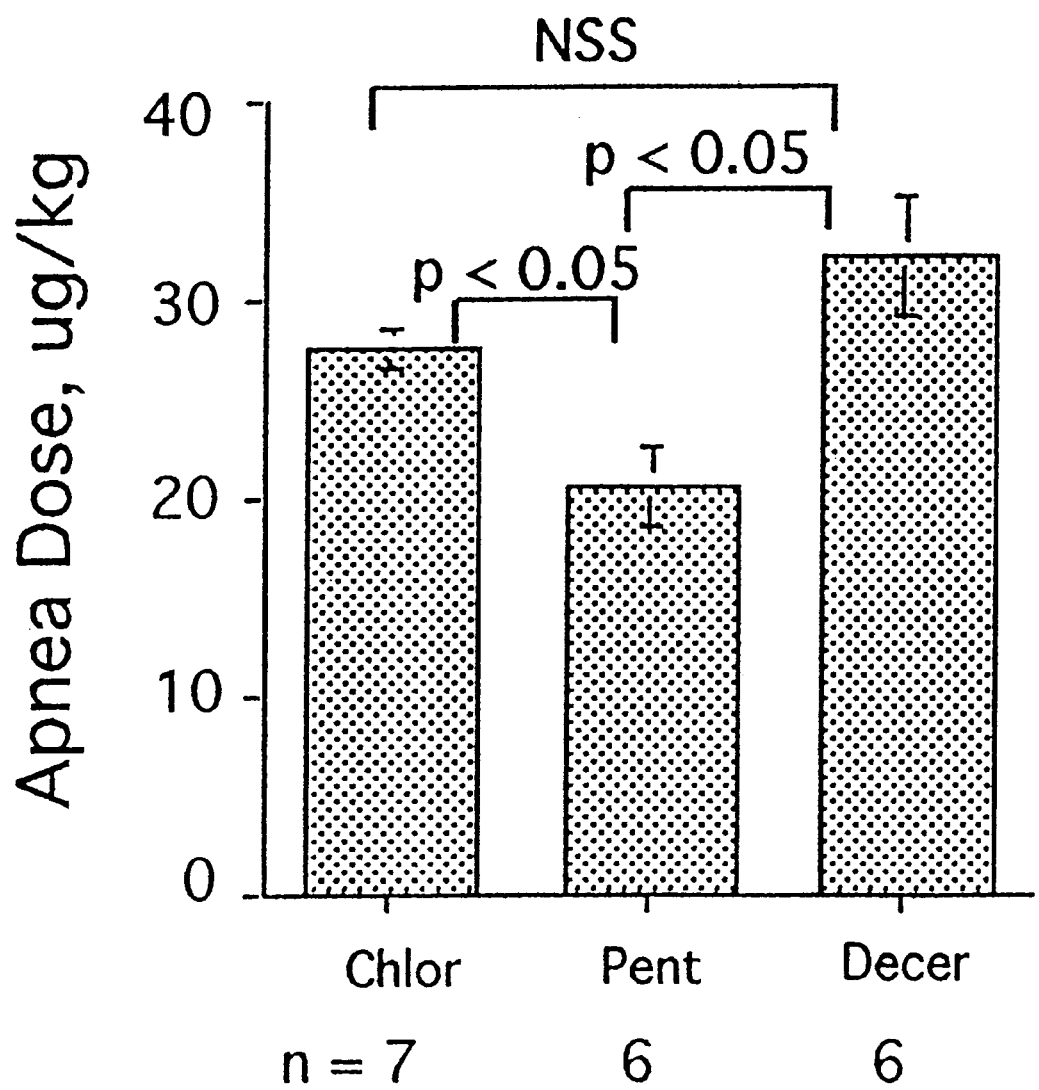
FIG. 2 is a series of histograms summarizing doses of fentanyl required to induce complete arrest of phrenic nerve activity (i.e., apnea) in chloralose-anesthetized cats (Chlor), pentobarbital-anesthetized cats (Pent), or in decerebrate, unanesthetized cats (Decer).

The following definitions and abbreviations are used throughout the specification. Those terms not expressly defined herein have their normal and accepted meaning with the relevant fields of medicine, physiology, and/or neurology.

"Agonist"=a compound that will bind to a receptor to form a complex which elicits a full pharmacological response, peculiar to the nature of the receptor involved.

"Antagonist"=a compound that will bind to a receptor to form a complex which does not give rise to any response and which hinders or prevents receptor occupancy by an otherwise effective agonist.

"cAMP-PKA"=cyclic adenosine monophosphate-protein kinase A.

"α-Chloralose"=1,2-O-(2,2,2-trichloroethylidene)-α-D-glucofuranose and salts thereof.

"(±)-Chloro-APB"=((+/−)6-chloro-7,8-dihydroxy-3-allyl-1-phenyl-2,3,4,5-tetrahydro-1H-3-benzazepine hydrobromide) (also known as SKF-82958).

"CNS"=central nervous system.

"DAMGO"=D-Ala$^2$,N-Me-Phe$^4$,Gly-ol$^5$-Enkephalin.

"$D_1$-Dopamine Receptor"=a dopamine-specific receptor located in the post-synaptic membrane. In humans, the $D_1$ receptor comprises a membrane-bound protein having 446 residues.

"$D_1$-Dopamine Receptor Agonist"=a generic term designating any agonist selective for the $D_1$ dopamine receptor. A non-limiting, illustrative list of $D_1$-dopamine receptor agonists includes (±)-SKF-38393, CY 208–243 (i.e., (−)-(6aR, 12bR)-4,6,6a,7,8,12b-hexahydro-7-methylindolo{4,3-a}phenanthridine), dihydrexidine hydrochloride (i.e., (±)-trans-10,11-dihydroxy-5,6,6a,7,8,12b-hexahydrobenzo-{a}phenanthridine) (all available commercially from Tocris Cookson Inc., Ellisville, Mo.), (±)-chloro-APB ((+/−)-6-chloro-7,8-dihydroxy-3-allyl-1-phenyl-2,3,4,5-tetrahydro-1H-3-benzazepine hydrobromide) (also known as SKF-82958), SKF 81297 ((+/−)-6-chloro-7,8-dihydroxy-1-phenyl-2,3,4,5-tetrahydro-1H-3-benzazepine) and ABT 431 (available from Abbott Laboratories, Abbott Park, Ill.). The definition encompasses the forms explicitly listed herein, plus individual enantiamers or diastereomers thereof (where applicable), racemic mixtures thereof, enantiomerically-enriched mixtures thereof, and pharmaceutically-accceptable salts of any of the above-mentioned forms.

"EPSC"=excitatory postsynaptic current.

"EPSP"=excitatory postsynaptic potential.

"E"=expiratory phase of phrenic nerve activity.

"Fentanyl"=N-phenyl-N-{1-(2-phenylethyl)-4-piperidinyl}propanamide and salts thereof.

"I"=inspiratory phase of phrenic nerve activity.

"Opiates" and "Opioids"=roughly synonymous terms that generically denotes a class of narcotic compounds characterized by having addiction-forming or addiction-sustaining properties similar to morphine or being capable of conversion into a drug having such addiction-forming or addiction-sustaining properties. Specifically, the term "opiates" denotes compounds containing the fundamental morphine or thebaine structure and possessing some affinity to any, or all, of the opioid receptor subtypes. Examples of opiates are heroin, buprenorphine, and naltrexone. An "opioid" is any compound, peptide or otherwise, which, while not containing the fundamental morphine or thebaine structure, possesses some affinity for any, or all, of the opioid receptor subtypes. Common opioids are endorphin, fentanyl and methadone. A non-exclusive list of opiates and opioids includes mophine, heroin, opium, cocaine, fentanyl, ecgonine, thebaine. Commercially-available opiates and opioids (and exemplary trademarked names, where available) include: alfentanil ("Alfenta"), buprenorphine ("Temgesic," "Subutex"), carfentanil ("Carfenta"), codeine, dihydrocodeine, diprenorphine, etorphine ("Immobilon"), fentanyl ("Sublimaze"), heroin, hydrocodone ("Vicodin"), hydromorphone ("Dilaudid"), LAAM ("Orlaam"), levorphanol ("Levo-Dromoran"), meperidine ("Demerol"), methadone ("Dolophine"), morphine, naloxone ("Narcan"), naltrexone ("Trexan"), beta-hydroxy 3-methylfentanyl, oxycodone ("Percodan"), oxymorphone ("Numorphan"), propoxyphene ("Darvon"), remifentanil ("Ultiva"), sufentanil ("Sufenta"), tilidine ("Valeron"), and tramadol ("Ultram"). The definition includes all opiates and opioids, from any source, including naturally-derived compounds, synthetic compounds, and semi-synthetic compounds. The definition also includes all isomers, stereoisomers, esters, ethers, salts, and salts of such isomers, steroeisomers, esters, and ethers, whenever the existence of such isomers, stereoisomers, esters, and ethers is possible within the specific chemical designation.

"Opioid Receptors"=a term used collectively to refer to the three well-defined or "classical" types of opioid receptors $\mu$, $\delta$, and $\kappa$. Genes encoding for these receptors have been cloned. Opioid receptors belong to the G-protein-coupled receptor superfamily and their ligands are the endogenous opioid peptides and opiate/opioid drugs. The concept that there is more than one type of opioid receptor arose to explain the dual actions of the synthetic opioid nalorphine, which antagonizes the analgesic effect of morphine in humans, but also acts as an analgesic in its own right. It was thus concluded that the analgesic action of nalorphine is mediated by a receptor, later called the κ-opioid receptor, that is different from the morphine receptor, $\mu$.

"PI"=postinspiratory phase of phrenic nerve activity.

"PN"=phrenic nerve activity.

"PNA"=phrenic nerve action potential.

"∫PN"=moving average of phrenic nerve action potential frequency activity.

"RAS"=reticular activating system.

"R-(+)-SCH-23390"=(R)(+)-7-chloro-8-hydroxy-3-methyl-1-phenyl-2,3,4,5-tetrahydro-1H-3-benzazepine (and salts thereof), a potent and selective $D_1$ dopamine receptor antagonist.

"(±)-SKF-38393"=(±)-1-phenyl-2,3,4,5-tetrahydro-(1H)-3-benzazepine-7,8-diol (and salts thereof), a potent and selective $D_1$ dopamine receptor agonist.

Introduction

Opioids exhibit several general features affecting respiration in mammals, including humans, which to date have not been analyzed mechanistically in laboratory animal studies. Thus, a goal of the present work was to analyze opioid-mediated respiratory disturbances at the cellular and systems levels and to determine if respiratory suppression might be abolished without affecting the analgesic or anesthetic effects of opioids. Included in the analysis is an evaluation of anesthetic influences on opiate respiratory effects. In short, these two effects (anesthesia and respiratory suppression) are regularly seen together during human and veterinary surgical procedures. A second objective was to determine whether opioid-mediated respiratory disturbances can be eliminated or alleviated by membrane receptor-activated mechanisms that do not alter agonist binding to opiate receptors. As detailed below, the inventor has found that administering $D_1$-dopamine receptor agonists in conjunction with opioids does, in fact, eliminate entirely (or significantly alleviate) the respiratory suppression exhibited by opioids, without compromising the anesthetic and/or analgesic effect of the opioid.

In the paragraphs to follow, reasons for choosing the in vivo feline respiratory network as a test system for this analysis are addressed, the influence of anesthesia and its ramifications are discussed, and cellular mechanisms that might account for opioid disturbances of respiration are considered. Note that while the mechanistic discussion included herein is the inventor's present understanding of why the invention functions as it does, the scope of the invention is not limited by the inventor's understanding of the underlying biochemical phenomena that give rise to the observed effects.

Cats as an Experimental in vivo Model for Humans

Cats were chosen as a test model because most of the fundamental knowledge of respiratory neural network properties has been obtained from studies carried out in this species (Long and Duffin, 1986). It must be noted, however, that opiates have the paradoxical behavioral effect of provoking marked excitation and rage in the awake cat (Shemano, Wendel and Ross, 1961).

Despite the unusual behavioral effects of opioids on cats, the respiratory effects of opioids seen in cats in the present study are similar to those in humans, monkeys, rabbits and dogs, but are dissimilar from those seen in rats. Opiates given to humans and dogs in sub-apneic doses depress depth and rate of breathing, as well as tidal exchange, with the greatest effect on rate being due to a prolongation of expiration (Jaffe and Martin, 1980). In monkeys, respiratory frequency, minute volume, and tidal volume are suppressed by morphine, heroin, and fentanyl (Kishioka, Ko and Woods, 2000). In the rabbit, morphine depresses peak integrated inspiratory discharge activity and decreases respiratory frequency by prolonging the expiratory period (Howard and Sears, 1990).

In adult rats in vivo, opioids also decrease breathing frequency and inspiratory airflow rate. But, in contrast to humans, dogs, etc. slowing of breathing in rats is due to prolongation of the inspiratory phase, rather than prolonged expiration (Fone and Wilson, 1986). Thus, the cat is an accurate model system for evaluating opioid effects on the respiratory neural network of humans, and data from such animal studies have clinical implications which are clearly applicable to humans.

Influence of Anesthesia on Opioid-Mediated Respiratory Effects

The respiratory neural network receives tonic excitatory drive from two predominant sources: from the brainstem and carotid body chemoreceptors, and from the reticular activating system (RAS; Richter, Ballantyne and Remmers, 1986). Most studies of opioid effects on respiratory neurons have been performed in anesthetized animals, even though both opioids and general anesthetics depress the RAS (Killam, 1968). Work leading to the present invention demonstrates that during pentobarbital anesthesia, which markedly depresses neurons of the RAS (Killam, 1968), fentanyl produced the largest variety of network disturbances (see Table 1, infra). The most distinguishing features of opioid respiratory depression during pentbarbital anesthesia were the significantly lower rate of inspiratory discharge augmentation and prolongation of inspiratory discharges. These effects most likely reflect additive effects of pentobarbital and fentanyl in reducing tonic RAS drive. Consequently, RAS depression could suppress recurrent excitation within pools of Aug-I neurons and thus delay activation of inspiratory off-switching neurons (Richter, 1996). Summation of depressant effects on tonic RAS drive could also explain why fentanyl evoked central apnea with the lowest range of doses in the pentobarbital-anesthetized cats (see FIG. 2).

α-Chloralose is reported to act cortically to release the reticular formation from inhibition (Winters, 1968) and to have minimal depressant effects on autonomic functions (Balis and Monroe, 1964). In the present work, during anesthesia with chloralose, fentanyl produced a smaller number of respiratory rhythm disturbances than during pentobarbital anesthesia. Also, PN activity was abolished with a potency that was similar in the unanesthetized decerebrate cat. The only difference between the effects of fentanyl in chloralose-anesthetized animals and decerebrate unanesthetized animals was a greater reduction in the frequency of burst discharges in the chloralose-anesthetized animals. It thus appears that α-chloralose has minimal influence on opioid respiratory actions and may be a good anesthetic for laboratory experiments that investigate opioid effects on the respiratory network. The chloralose-anesthetized animal model has the advantage over the unanesthetized decerebrate animal model in being easier and quicker to prepare.

Mechanisms and Sites of Action Related to the Effects of Fentanyl on Phrenic Nerve Activity and Medullary Respiratory Neurons It is well established that selective µ-opioid receptor agonists such as fentanyl depress the excitability of many types of neurons by increasing membrane permeability to potassium ions with consequent MP hyperpolarization, and decreasing current through voltage-gated membrane calcium channels (North, Williams, Surprenant and Christie, 1987). These cellular mechanisms may be responsible for the depression of inspiratory bulbospinal neurons seen in the present work and for similar effects of opioids applied directly to various bulbar respiratory neurons by iontophoresis in other studies (Denavit-Saubie', Champagnat and Zieglgansberger, 1978).

Analysis of the effects of iontophoretically applied DAMGO on the discharge properties of Aug-I bulbospinal neurons indicates that the cells were depressed postsynaptically by the μ-opioid receptor agonist. DAMGO shortened burst duration, reduced spike frequency and prolonged the silent interval between bursts. The depression might be reflected through the network of inspiratory neurons, which are mutually excitatory (Cohen, 1979) and form positive feedback loops (Richter, 1996), to result in a more prolonged and more gradually augmenting PN discharge (see Table 1, infra). DAMGO iontophoresis also increased the amplitude of extracellularly recorded action potentials, which could be the result of postsynaptic MP hyperpolarization. A postsynaptic site of action is consistent with reports that opiates hyperpolarize membrane potential of some medullary inspiratory neurons in vitro (Ballanyi et al, 1997), and depress spontaneous and glutamate-evoked postsynaptic discharges of extracellularly-recorded bulbar inspiratory neurons in vivo (Denavit-Saubie' et al., 1978). Opioids also presynaptically depress inspiratory neurons, other types of brain stem respiratory neurons (Johnson et al, 1996), and non-rhythmic medullary chemoreceptor neurons (Trouth et al. 1993). By whatever associated mechanisms, decreases in excitability of inspiratory neurons with associated changes in contractility of diaphragmatic, chest wall, and accessory muscles can account to a large measure for the depression of tidal volume produced by μ- and δ-receptor selective opioid drugs (Shook et al, 1990).

On phrenic nerve activity, the most consistent effect of fentanyl was the prolongation of the expiratory silent period. In the lowest effective doses, the lengthening occurred with minimal effects on PN discharge properties. This suggests that neurons which control the discharge interval of Aug-I neurons, such as expiratory neurons of the Boetzinger Complex (Duffin, Tian and Peever, 2000) became somehow more effective in the presence of low doses of fentanyl.

On Aug-E neurons of the caudal medulla, fentanyl had several effects that occurred without significant change of neuronal input resistance. The lack of a significant effect on input resistance is taken as evidence for opioid actions on Aug-E neurons at remote dendritic sites that are too distant to be detected by a microelectrode in the soma and are beyond the reach of somatically-applied current pulses (Kreuter, Richter, Camerer and Senekowitsch, 1977). The membrane hyperpolrization and outward current measured following larger doses of fentanyl in the present study may represent flow of positive ions from the soma to distal dendritic sites where activation of μ-opioid receptors hyperpolarizes membrane potential. Convincing evidence for such a mechanism was uncovered in the Locus Coeruleus, where opioids exert substantial inhibitory effects through actions at distal dendritic synapses (Travagli, Wessendorf and Williams, 1996). In the respiratory network, morphological and electrical measurements (Kreuter et al., 1977) have shown that medullary respiratory neurons, including Aug-E neurons, receive significant tonic synaptic input at remote regions of the dendritic tree as well as on the proximal dendrites and soma. At such remote synapses, opioids might modulate membrane conductances of Aug-E neurons postsynaptically and depress neurotransmitter release presynaptically. Indeed, voltage clamp measurements (See FIGS. 6A through 6F) revealed that fentanyl has presynaptic inhibitory actions as evidenced by the reduction in EPSP and EPSC frequency.

In order of increasing dose, the effects of fentanyl on caudal Aug-E neurons were: depression of the amplitude of depolarizing synaptic drive potential with reduction of discharge intensity; prolongation of the drive potentials and elimination of action potentials; loss of respiratory rhythmicity with membrane depolarization and low-frequency firing; and membrane hyperpolarization that was greater than maximum control levels.

The depression of excitatory synaptic drive potentials at the lowest doses probably reflects postsynaptic inhibition of caudal Aug-E neurons, as well as presynaptic depression of chemoreceptor and reticular formation neurons that provide what appears to be the only excitatory drive to caudal Aug-E neurons (Ezure, 1990). Higher doses prevented periodic MP hyperpolarization, ostensibly through presynaptic depression of preinspiratory, inspiratory and postinspiratory neurons (Richter, 1996). Coupled with a persistence of sufficient tonic excitatory synaptic input to Aug-E neurons, this may have led to the prolonged low-intensity discharges. Extended discharges of caudal medullary expiratory neurons in chloralose-anesthetized dogs (Laubie et al., 1986) and expiratory intercostal nerve discharges in decerebrate or chloralose-urethane-anesthetized rabbits (Howard and Sears, 1990) following opioid administration have been reported. Such discharges explain why opioids can cause chest wall rigidity that impairs effective ventilation during induction of anesthesia (Marty and Desmonts, 1981). Because firing was terminated occasionally for brief intervals in the present study during feeble bursts of phrenic nerve activity, it seems some residual inhibition from inspiratory neurons remained (Richter, 1996). The largest doses of fentanyl, which affected steady membrane hyperpolarization and depression of inward current (FIGS. 6A through 6F), may have blocked all or most of the excitatory drive from RAS and chemoreceptor neurons.

The postinspiratory neurons tested in this work were very sensitive to depression by fentanyl. Two types of PI neurons have been identified in the medulla, those with axonal projections in cranial nerves to the upper airways, and those which are not antidromically activated by cranial nerve or spinal cord stimulation (Bianchi et al., 1995). The latter may be a type of PI neuron that irreversibly terminates inspiration during each respiratory cycle through synaptic depression of bulbar Aug-I neurons (Richter, 1996). Depression of this type of PI neurons by fentanyl could have contributed to the prolongation of the augmenting component of phrenic nerve discharges in the present study (see FIG. 8B).

Reversal of Opioid-Mediated Respiratory Depression by $D_1$-Dopmine Receptor Agonists The most likely cellular transduction mechanism leading to μ-opioid receptor-mediated inhibition of respiratory neurons involves depression of the cAMP-PKA signaling pathway, as has been described for a variety of CNS neurons (Xie and Lewis, 1997). The excitability of medullary respiratory neurons is increased when the adenylyl cyclase-cAMP-PKA system is up-regulated (Lalley, Bischoff, Pierrefiche and Richter, 1997). Thus, $D_1$-agonists seem to produce a generalized increase in excitability within the isolated bulbospinal nervous system of the neonatal rat. In the work leading to the present invention, only neural discharges from the respiratory network were monitored, so conclusions regarding effects on other somatic motor pathways cannot be made. It seems, however, that if vagal and sympathetic cardiovascular efferent pathways are stimulated, the effect is relatively short-lasting, i.e., not more than about 30 seconds judging from the effects of the highest effective doses (3 mg/kg) of (±)-chloro-APB or (±)-SKF-38393 on blood pressure (see Examples for further discussion).

The work performed to date has not identified the mechanism(s) responsible for the respiratory effects of the $D_1$-agonists. The mechanism does not, however, appear to involve increased sensitivity of brainstem or carotid body chemoreceptor mechanisms. Other possibilities include postsynaptic excitatory modulation of respiratory neurons, or increased presynaptic excitation by actions within the RAS.

Pharmaceutical Dosage Forms

Another aspect of the invention provides pharmaceutical compositions for inducing analgesia or anesthesia while simultaneously minimizing respiratory suppresion, the composition comprising an opiate or opioid compound (including pharmaceutically-acceptable salts thereof), admixed with a $D_1$ dopamine receptor agonist, in combination with an acceptable carrier therefor and optionally in combination with other therapeutically-active ingredients or inactive accessory ingredients. The carrier must be pharmaceutically-acceptable in the sense of being compatible with the other ingredients of the formulation and not deleterious to the recipient. The pharmaceutical compositions include those suitable for oral, topical, inhalation, rectal or parenteral (including subcutaneous, intramuscular and intravenous) administration.

Regarding pharmaceutically-acceptable salts, these include acid addition salts such as those made from inorganic acids such as hydrochloric acid, nitric acid, and the like, or from organic acids such as citric acid, lactic acid, and the like. The salts also include, where appropriate, salts made with bases, such as sodium and potassium hydroxide. The salts comprehended by the invention are made by conventional methods well known to those skilled in the art. The salts for therapeutic use of the subject pharmaceutical compositions are pharmaceutically-acceptable salts, as are well understood in the art.

The compounds may also be administered in the form of individual enantiomers or diastereomers (where applicable), or racemic mixtures thereof, or enantiomerically- or diastereomerically-enriched mixtures, as well as pharmaceutically-acceptable salts of any of these forms.

The formulations may conveniently be presented in unit dosage form and may be prepared by any of the methods well known in the art of pharmacy. The term "unit dosage" or "unit dose" is denoted to mean a predetermined amount of the active ingredients sufficient to be effective for inducing analgesia or anesthesia in a mammalian subject (human or non-human). Making each type of pharmaceutical composition described herein includes the step of bringing the active compounds into association with a carrier and one or more optional accessory ingredients. In general, the formulations are prepared by uniformly and intimately bringing the active compounds into association with a liquid or solid carrier and then, if necessary, shaping the product into the desired unit dosage form.

Formulations of the present invention suitable for oral administration may be presented as discrete units such as capsules, cachets, tablets, boluses or lozenges, each containing a predetermined amount of the active compounds; as a powder or granules; or in liquid form, e.g., as an aqueous solution, suspension, syrup, elixir, emulsion, dispersion, or the like.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients, e.g., binders, lubricants, inert diluents, surface active or dispersing agents. Molded tablets may be made by molding in a suitable machine a mixture of the powdered active compounds with any suitable carrier.

Formulations suitable for parenteral administration conveniently comprise a sterile preparation of the active compound in, for example, water for injection, saline, a polyethylene glycol solution and the like, which is preferably isotonic with the blood of the recipient.

Useful formulations also comprise concentrated solutions or solids containing the active compounds, which upon dilution with an appropriate solvent give a solution suitable for parenteral administration.

Preparations for topical or local applications comprise aerosol sprays, lotions, gels, ointments, suppositories etc., and pharmaceutically-acceptable vehicles therefor, such as water, saline, lower aliphatic alcohols, polyglycerols such as glycerol, polyethylene glycerol, esters of fatty acids, oils and fats, silicones, and other conventional topical carriers. In topical formulations, the subject compounds are preferably utilized at a concentration of from about 0.1% to 5.0% by weight.

Compositions suitable for rectal administration comprise a suppository, preferably bullet-shaped, containing the active ingredients and pharmaceutically-acceptable vehicles therefor such as hard fat, hydrogenated cocoglyceride, polyethylene glycol and the like. In suppository formulations, the subject compounds are preferably utilized at concentrations of from about 0.1% to 10% by weight.

Compositions suitable for rectal administration may also comprise a rectal enema unit containing the active ingredient and pharmaceutically-acceptable vehicles therefore such as 50% aqueous ethanol or an aqueous salt solution which is physiologically compatible with the rectum or colon. A rectal enema unit consists of an applicator tip protected by an inert cover, preferably comprised of polyethylene, lubricated with a lubricant such as white petrolatum and preferably protected by a one-way valve to prevent back-flow of the dispensed formula, and of sufficient length, preferably two inches, to be inserted into the colon via the anus. In rectal formulations, the subject compounds are preferably utilized at concentrations of from about 5.0–10% by weight.

Useful formulations also comprise concentrated solutions or solids containing the active ingredients, which upon dilution with an appropriate solvent, preferably saline, give a solution suitable for rectal administration. The rectal compositions include aqueous and non-aqueous formulations that may contain conventional adjuvants such as buffers, bacteriostats, sugars, thickening agents, and the like. The compositions may be presented in rectal single dose or multi-dose containers, for example, rectal enema units.

Preparations for topical or local surgical applications for treating a wound comprise dressings suitable for wound care. In both topical or local surgical applications, the sterile preparations of the active ingredients are preferably utilized at concentrations of from about 0.1% to 5.0% by weight applied to a dressing.

Compositions suitable for administration by inhalation include formulations wherein the active ingredients are solids or liquids admixed in a micronized powder having a particle size in the range of about 5 microns or less to about 500 microns, or liquid formulations in a suitable diluent. These formulations are designed for rapid inhalation through the oral passage from a conventional delivery system such as inhalers, metered-dose inhalers, nebulizers, and the like. Suitable liquid nasal compositions include conventional nasal sprays, nasal drops and the like, of aqueous solutions of the active ingredient(s).

In addition to the aforementioned ingredients, the formulations of this invention may further include one or more optional accessory ingredient(s) utilized in the art of pharmaceutical formulations, i.e., diluents, buffers, flavoring agents, colorants, binders, surface active agents, thickeners, lubricants, suspending agents, preservatives (including antioxidants) and the like.

The amount of opiate/opioid and $D_1$ dopamine receptor agonist required to be effective for any indicated condition will, of course, vary with the individual mammal being treated and is ultimately at the discretion of the medical or veterinary practitioner. The factors to be considered include the condition being treated, the route of administration, the nature of the formulation, the mammal's body weight, surface area, age and general condition, the particular composition to be administered, and the desired level of analgesia or anesthesia to be achieved. In general, a suitable effective dose is in the range of about 0.01 to about 50 mg/kg body weight per day, preferably in the range of from about 0.1 to about 10 mg/kg per day, and more preferably still 1.0 to 5.0 mg/kg per day, calculated as the non-salt form of the $D_1$-dopamine receptor agonist in the formulation. The total daily dose may be given as a single dose, multiple doses, e.g., two to six times per day, or by intravenous infusion for a selected duration. Dosages above or below the range cited above are within the scope of the present invention and may be administered to the individual patient if desired and necessary.

In general, the pharmaceutical compositions of this invention contain from about 0.5 mg to about 1.5 g active ingredient per unit dose and, preferably, from about 7.5 to about 1000 mg per per unit dose. If discrete multiple doses are indicated, treatment might typically be 100 mg given from two to four times per day.

Analgesic and/or anesthetic compositions according to the present invention may be administered prophylactically, chronically, or acutely. For example, such compounds may be administered prophylactically to patients exhibiting chronic pain. The subject compounds may also be administered prophylactically, as in the case of administering anesthesia prior to a planned medical procedure, or acutely, for example, when treating traumatic injuries where the patient is still conscious and in great pain.

EXAMPLES

The following examples are included solely to provide a more thorough understanding of the invention disclosed herein. The Examples do not limit the invention described and claimed herein in any fashion.

Preparation of Animals

Experiments were performed on 28 cats in the Department of Physiology, University of Wisconsin, Madison, Wis., and on 1 cat in the II. Institute of Physiology, University of Goettingen, Germany. Animals of either sex, 3.0 to 5.5 kg were used. Care and use of the animals were in accordance with the guiding principles of the University of Wisconsin Animal Care Committee and the American and German Physiological Societies. Animals were either anesthetized with pentobarbital sodium (Abbott Laboratories, North Chicago, Ill., or CEVA E. G., Hannover, Germany: 30 mg/kg i.v. or 40 mg/kg i.p. initially, followed by 4–12 mg/hr, i.v) or α-chloralose (50–60 mg/kg i.v.). Pentobarbital and chloralose administration was preceded by induction with halothane in an anesthetic chamber (5% halothane in oxygen, 5L/min gas flow) followed by administration through a mask (2.5–3.5%, 2–3L/min). Levels of anesthesia were sufficient to produce and maintain a state free of pain and discomfort. Supplemental i.v. doses of pentobarbital or chloralose were given if systolic arterial pressure increased spontaneously or if discharges of phrenic nerve activity decreased in duration and increased in frequency or showed a tonic discharge component. Additional anesthetic was also given if surgical procedures or pressure on a paw produced withdrawal reflexes and increases of heart rate, blood pressure or frequency of phrenic nerve discharges.

Halothane was also administered during midcollicular decerebration, using the procedures described in detail by Kirsten and St. John, 1978. During anesthesia, the external carotid arteries were ligated, the brain stem was transected between the superior and inferior colliculi and brain tissue rostral to the transection was removed by aspiration. After halothane was discontinued, decerebrate rigidity was evident in all animals. None of the animals exhibited nociceptive withdrawal reflexes or changes of blood pressure or phrenic nerve discharge patterns that would indicate the presence of pain or discomfort. Body temperature was maintained at 36–38° C. by external heating. Atropine sulfate (Sigma-Aldrich, St. Louis, Mo., or B. Braun, Melsugen, Germany; 0.2 mg/kg, i.v.) was administered to prevent salivation and dexamethasone (American Regent Laboratories, Shirley, N.Y. or Ratiopharm, GMBH, Ulm, Germany; 0.3 mg/kg) was given to prevent brain edema. Experiments were terminated by intravenous injection of sodium pentobarbital in sufficient quantity to produce irreversible cardiac arrest.

A femoral artery and both femoral veins were cannulated for monitoring arterial pressure and administering Glucose-Ringer's solution and drugs. A cannula was inserted into the trachea below the larynx. Neuromuscular paralysis was achieved by intravenous administration of gallamine triethiodide (American Cyanamid Co., Pearl River, N.Y. or Specia Rhone-Poulenc Rorer, Paris, France; 4–8 mg/kg initially, followed by 4–8 mg/hr). Animals were ventilated with oxygen-enriched air (65–75 vol. % $O_2$) through a tracheal cannula. End-tidal $CO_2$ was maintained at 3.5–4.5 vol %, except during tests of the sensitivity of the respiratory network to $CO_2$, by adjusting ventilatory rate and tidal volume. Ventilatory pump frequency, end-tidal $CO_2$ and inspired $O_2$ were monitored continuously (NormocapOxy, Datex-Ohmeda, Madison, Wis.). A pneumothorax was performed bilaterally to increase stability of recording from medullary respiratory neurons. Atelectasis was prevented by applying 1–2 cm $H_2O$ positive pressure to the expiratory airflow.

Animals were mounted rigidly in a stereotaxic head holder and spinal frame. Phrenic nerves ($C_{4-5}$ branches) and cervical vagus nerves were exposed bilaterally through a dorsal approach, sectioned, their central ends desheathed and mounted on bipolar silver hook electrodes. The head of the animal was ventroflexed to allow wide exposure of the dorsal surface of the medulla by occipital craniotomy. The dura and arachnoid membranes were removed from the medulla, and patches of pia membrane were removed to allow insertion of fine-tipped glass microelectrodes. A pressure foot was placed gently on the surface of the medulla over the site of microelectrode insertion. A cervical laminectomy ($C_2$–$C_4$) was performed and the dura was cut and reflected for insertion of an electrode array to simulate the cervical reticulospinal tracts bilaterally for identification of bulbospinal neurons.

Recording Procedures

Phrenic nerve activity (PNA) was amplified (2,000–10,000 X; Grass Instruments, Quincey, Mass. or npi electronics, Tamm, Germany), band-pass filtered (80–3,000 Hz), displayed on an oscilloscope (Tektronix Instruments, Beaverton, Oreg.) and registered on magnetic tape (frequency response, DC-5 kHz; Vetron Technology Inc., Rebersburg, Pa. or Racal, Southampton, United Kingdom) and chart recorder paper (DC-10 KHz; Gould, Cleveland, Ohio) as raw discharges and as moving averages (τ=100 ms) of action potential frequency.

Intracellular recordings were obtained from medullary expiratory bulbospinal neurons in the medulla caudal to the obex that exhibited augmenting membrane potential and discharge patterns (Aug-E neurons). The neurons were found 2.5–3.0 mm lateral to the midline and 1.7–2.8 mm below the dorsal surface. Recordings were made with fine-tipped glass micropipettes filled with 2M potassium methylsulfate and 5 mM BAPTA. DC resistance of the microelectrodes ranged from 50 to 80 MΩ. Membrane potentials were recorded in current clamp mode with amplifiers for intracellular recording (Bandwidth, DC –10,000 Hz; SEC 05; npi, Tamm, Germany or Dagan 8500, St. Paul, Minn.). Neuron input resistance (Rn) measurements were made by injecting 60 or 80 ms negative constant current pulses through the microelectrode and recording the resulting hyperpolarizing voltage drop across the cell membrane. Voltage clamp measurements of membrane currents were made during discontinuous voltage clamp (switching frequency 25–30 KHz, 25% duty cycle) as described previously (Richter, Pierrefiche, Lalley and Polder, 1996). Electrophysiological data was also acquired and stored on a computer and CD with PowerLab hardware and software (AD Instruments, Castle Hill, NSW, Australia).

Bulbospinal inspiratory neurons with augmenting discharge patterns (Aug-I neurons) in the ventral respiratory group of the medulla (VRG; 2.5–3.5 mm rostral to the obex, 2.7–3.5 lateral to the midline, 2.7–4.5 mm ventral) were recorded extracellularly with 5-barrel microelectrode assemblies that were also used for iontophoresis. The electrode assemblies were prepared by heat-pulling pre-fabricated 5-barrel multipipette blanks (World Precision Instruments, Sarasota, Fla.) on a vertical pipette puller (Narishige PE-2, Tokyo, Japan) and breaking the tips back to a total diameter of 8–10 μm after back-filling the recording barrel with 4M NaCl (resistance, 5–10 MΩ) and the iontophoresis barrels with drug solutions and current-balancing electrolyte. Extracellular discharges of I-neurons were recorded with a bridge current clamp amplifier (DAGAN 8500, St. Paul, Minn.), amplified 1000 X and bandpass filtered at 100–3000 Hz (Grass P511 preamplifier, Quincy, Mass.), monitored on an oscilloscope and recorded as raw discharges and moving averages on the chart recorder.

Postinspiratory neurons rostral to the obex in the VRG were recorded extracellulary with single glass micropipettes, tip diameter 2–3 μm, filled with 2M NaCl (5–10 MΩ).

Identification of Bulbospinal Respiratory Neurons

Two concentric coaxial electrodes (SNEX-100, A-M Systems, Inc., Everett, Wash.) were positioned bilaterally in the cervical reticulospinal tracts at the $C_3$ level. Stimulation with single shocks applied bilaterally (5–10V, 50 μs pulse duration) evoked a maximal, short-latency orthodromic volley of PNA after each single shock. The single shocks were also sufficient to activate bulbospinal expiratory and inspiratory neurons by antidromic conduction of action potentials, as verified by collision with spontaneous action potentials.

Iontophoresis

Chemicals for iontophoretic application were dissolved in double-distilled water and adjusted to pH 4.5 with 0.1N HCl. Iontophoresis barrels contained: (i) the selective μ-opioid receptor agonist D-Ala$^2$,N-Me-Phe$^4$,Gly-ol$^5$-Enkephalin (DAMGO, purchased from Research Biochemicals International Natick (RBI), Natick Mass.), 10 mM in aqueous solution containing 1 mg/ml bovine serum albumin to prevent adherence of peptide to glass; (ii) the μ-opioid receptor blocker naloxonazine (RBI), 10 mM; (iii) the δ-opioid receptor blocker naltrindole (RBI), 10 mM; (iv) 165 mM NaCl for iontophoresis current balancing; (iv) control tests were also made with 165 mM NaCl, pH 4.5. Chemicals were retained with 5 nA anionic current and ejected with 50–90 nA cationic currents by a programmable iontophoresis current generator (Dagan 6400, St. Paul, Minn.). The iontophoresis protocol involved application of DAMGO several times with different ejecting currents and intervening recovery periods. After DAMGO had produced significant depression of neuronal discharges in several test runs, an opioid receptor blocker was iontophoresed concurrently for several minutes. After a recovery period this was followed by re-application of DAMGO in the absence of receptor blocker.

Intravenous Drug Administration

All drugs for intravenous injection were dissolved in Ringer's solution and injected slowly over a period of about 30 seconds to minimize changes of blood pressure and avoid loss of stable microelectrode recording. Drugs administered intravenously were: the μ-opioid receptor agonist fentanyl citrate; the p-opioid receptor antagonist naloxonazine; the $D_1$-Dopamine receptor agonists (±)-chloro-APB and (±)-SKF-38393; the $D_1$-dopamine receptor antagonist R-(+)-SCH-23390; and doxapram hydrochloride, a respiratory stimulant acting on carotid body chemoreceptors. Naloxonazine was purchased from RBI; doxapram was purchased from A-H-Robins, Richmond, Va. All other chemicals were purchased from Sigma Chemical Co., St. Louis, Mo.

To evaluate the dose-related effects of fentanyl, doses were given in increments ranging from 2.5 to 20 μg/kg.

Statistical Analysis

SigmaPlot version 4.11 software (Jandel Scientific, a division of SPSS Science, Chicago, Ill.) was used to obtain the mean and standard error of means of pooled data and to perform paired t-tests for significance of difference. Differences were accepted as significant if $p<0.05$.

EXAMPLE 1

Effects of Systemically-Administered Fentanyl on Respiratory Motor Output

Discharges of the phrenic nerve (PN) were measured as an index of how different doses of the μ-opioid agonist fentanyl given intravenouly alter activity of the bulbospinal respiratory networks in the different types of prepared animals (chloralose- or pentobarbital-anesthetized cats or unanesthetized decerebrate cats). In doses ranging from 7.5 to 15 μg/kg, fentanyl disturbed the control respiratory rhythm and depressed discharge intensity. Larger doses (20–40 μg/kg) abolished PN discharges (central apnea).

See FIGS. 1A through 1F. FIGS. 1A through 1F illustrate typical disturbances of respiratory rhythm caused by administering fentanyl intravenously in cats anesthetized with either pentobarbital (FIG. 1A=control, FIG. 1B=after administration of fentanyl); α-chloralose (FIG. 1C=control, FIG. 1D=after administration of fentanyl); or in unanesthetized decerebrate cats (FIG. 1E=control, FIG. 1F=after administration of fentanyl). Records in each panel show raw phrenic nerve activity (PN) and the moving average of phrenic nerve action potential frequency activity (∫PN), time constant 100 mSec. Symbols I, PI, and E in FIG. 1A denote the inspiratory, postinspiratory and expiratory phases of PN. Doses of fentanyl were 10 μg/kg in the pentobarbital- and α-chloralose-anesthetized cats, 12.5 μg/kg in the decerebrate cat.

Examples of disturbed PN rhythm produced by fentanyl in anesthetized and unanesthetized decerebrate animals are illustrated in FIGS. 1A through 1F and summarized in Table 1. Disturbances of respiratory rhythm consisted of a greatly prolonged expiratory phase silent period, decreased frequency of inspiratory (augmenting) and postinspiratory (declining) PN discharges, decreased peak action potential frequency at the end of the augmenting discharge and a reduced rate of action potential augmentation. In pentobarbital-anesthetized cats (FIGS. 1A and 1B) but not in the other prepared animals, the duration of the augmenting inspiratory discharge component was also significantly prolonged (p<0.05). Pentobarbital anesthesia also rendered the animals more susceptible to apnea.

The μ-opioid receptor blocker naloxonazine was tested on responses of 15 inspiratory neurons to DAMGO. The δ-opioid receptor blocker naltrindole was also tested on ten of the cells. Naloxonazine (50–90 nA) blocked DAMGO-mediated depression in all neurons tested. In the presence of Naloxonazine, DAMGO-mediated depression was reduced from 50–85 percent to 20–35 percent. When spike frequency was restored by naloxonazine, spike amplitude returned to control levels. Naltrindole (50–100 nA), on the other hand, was without effect on all neurons tested.

TABLE 1

EFFECTS OF FENTANYL ON PHRENIC NERVE DISCHARGE PROPERTIES

| | Decerebrate | | Chloralose | | Pentobarbital | |
|---|---|---|---|---|---|---|
| | Con | Fent (14.0 ± 2.7 μg/kg) | Con | Fent (12.0 ± 2.7 μg/kg) | Con | Fent (12.7 ± 4.3 μg/kg) |
| $T_I$ (Sec) | 1.76 ± 0.15 | 1.69 ± 0.10 | 1.73 ± 0.13 | 2.20 ± 0.35 | 1.61 ± 0.11 | 2.17* ± 0.27 |
| $T_{pI}$ (Sec) | 1.53 ± 0.14 | 1.18 ± 0.20 | 0.88 ± 0.14 | 1.24 ± 0.26 | 0.85 ± 0.22 | 0.94 ± 0.20 |
| $T_E$ (Sec) | 2.02 ± 0.29 | 3.61* ± 0.62 | 2.64 ± 0.21 | 4.55* ± 0.71 | 1.62 ± 0.32 | 4.16* ± 2.38 |
| $F_B$ ($min^{-1}$) | 13.22 ± 1.54 | 10.08 ± 1.17 | 11.45 ± 0.55 | 7.34* ± 0.58 | 15.25 ± 0.96 | 10.20* ± 1.07 |
| $F_S$ ($sec^{-1}$) | 897 ± 41.9 | 674* ± 69.3 | 719 ± 88.3 | 438* ± 63.9 | 661 ± 97.0 | 484* ± 88.4 |
| $^aF_S/^aT$ ($sec_{-2}$) | 604 ± 13.8 | 230* ± 15.0 | 735 ± 85.1 | 469* ± 31.0 | 1019 ± 121.2 | 417* ± 121.2 |

Fent = Fentanyl
$T_I$ = Inspiratory time
$T_{pI}$ = Postinspiratory time
$T_E$ = Expiratory time
FB = Burst frequency
$F_S$ = Spike Frequency
$\Delta F_S/\Delta T$ = Rate of spike augmentation during $T_I$
*Differences in responses between control and fentanyl treatment statistically significant, p ≤ 0.05

The histogram shown in FIG. 2 illustrates that significantly lower (p<0.05) doses of fentanyl were required to abolish PNA in pentobarbital-anesthetized cats (20+2.3 μg/kg) than in chloralose-anesthetized cats (27.4±0.9 μg/kg) or in unanesthetized decerebrate cats (31.1±2.9 μg/kg).

EXAMPLE 2

Figure 3A:
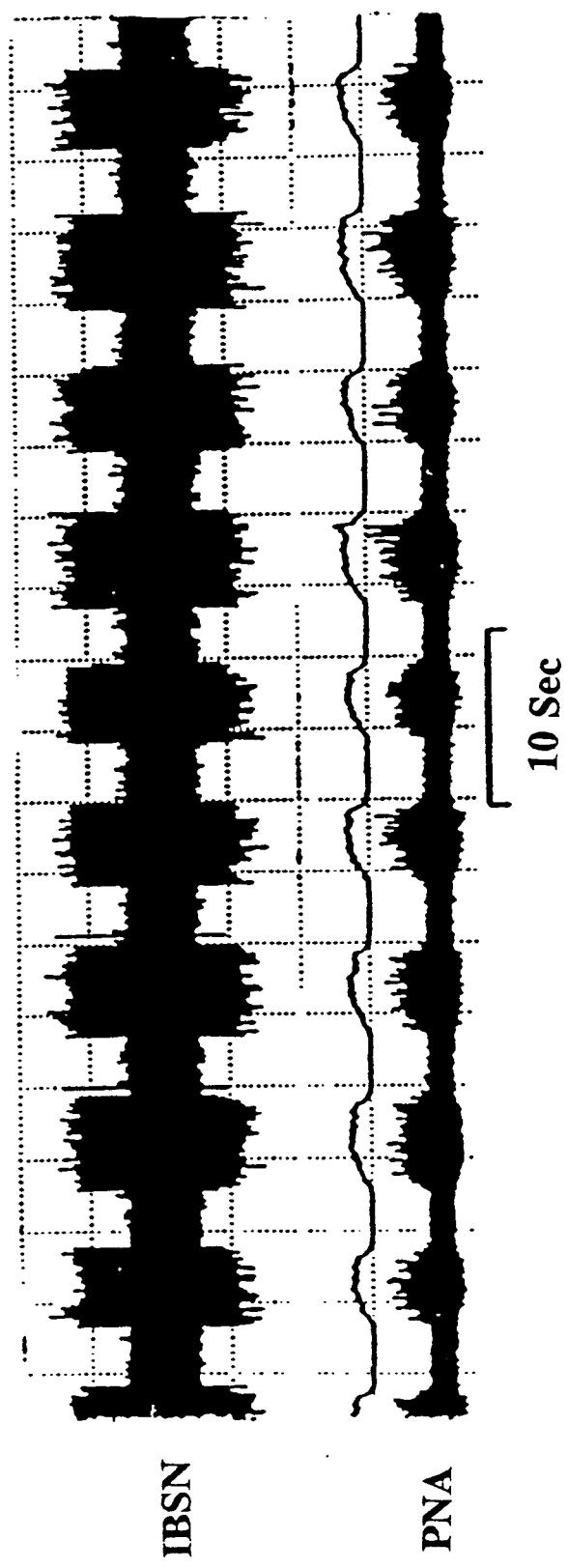

Iontophorsis of the μ-Receptor Agonist DAMGO Depresses Excitability of Bulbospinal Inspiratory Neurons Phrenic motoneurons receive excitatory synaptic input from bulbospinal Aug-I neurons located within the VRG of the medulla (Fedorko, Hoskin and Duffin, 1989). Thus, opioid-sensitive synapses on Aug-I neurons are potential sites where μ-opioids disrupt the PN rhythm and reduce discharge intensity. To test this possibility, DAMGO was applied directly to 25 antidromically-identified bulbospinal Aug-I neurons of the VRG by iontophoresis in eight pentobarbital-anesthetized cats. Under control conditions, the neurons exhibited robust bursts of action potentials that coincided with, or shortly followed, the onset of inspiratory PNA bursts (FIG. 3A). Iontophoresis of DAMGO depressed discharges of all Aug-I neurons.

Iontophoretic application of DAMGO for 1–3 minutes with 50–90 nA ejecting currents reduced action potential frequency to 50–85% of control. In addition, DAMGO further delayed the onset of discharges with respect to PNA, so that burst durations were shortened. In ten neurons, spike amplitudes were also increased during DAMGO application (FIG. 3B series). During recovery, control activity was restored within 60–90 seconds.

EXAMPLE 3

Dose-Dependent Effects of Systemically-Administered Fentanyl on Aug-E Bulbospinal Neurons The effects of fentanyl on membrane potential and discharge properties were measured in 12 bulbospinal Aug-E neurons in 11 cats. In two additional cats, effects on membrane currents were also measured in two Aug-E neurons during voltage clamp. Eight cats were anesthetized with pentobarbital, six with α-chloralose. Doses of 5–120 μg/kg fentanyl were given in 2.5–20 μg/kg increments. The dose-related effects on Aug-E neurons were similar in the presence of either anesthetic.

Figure 4A:
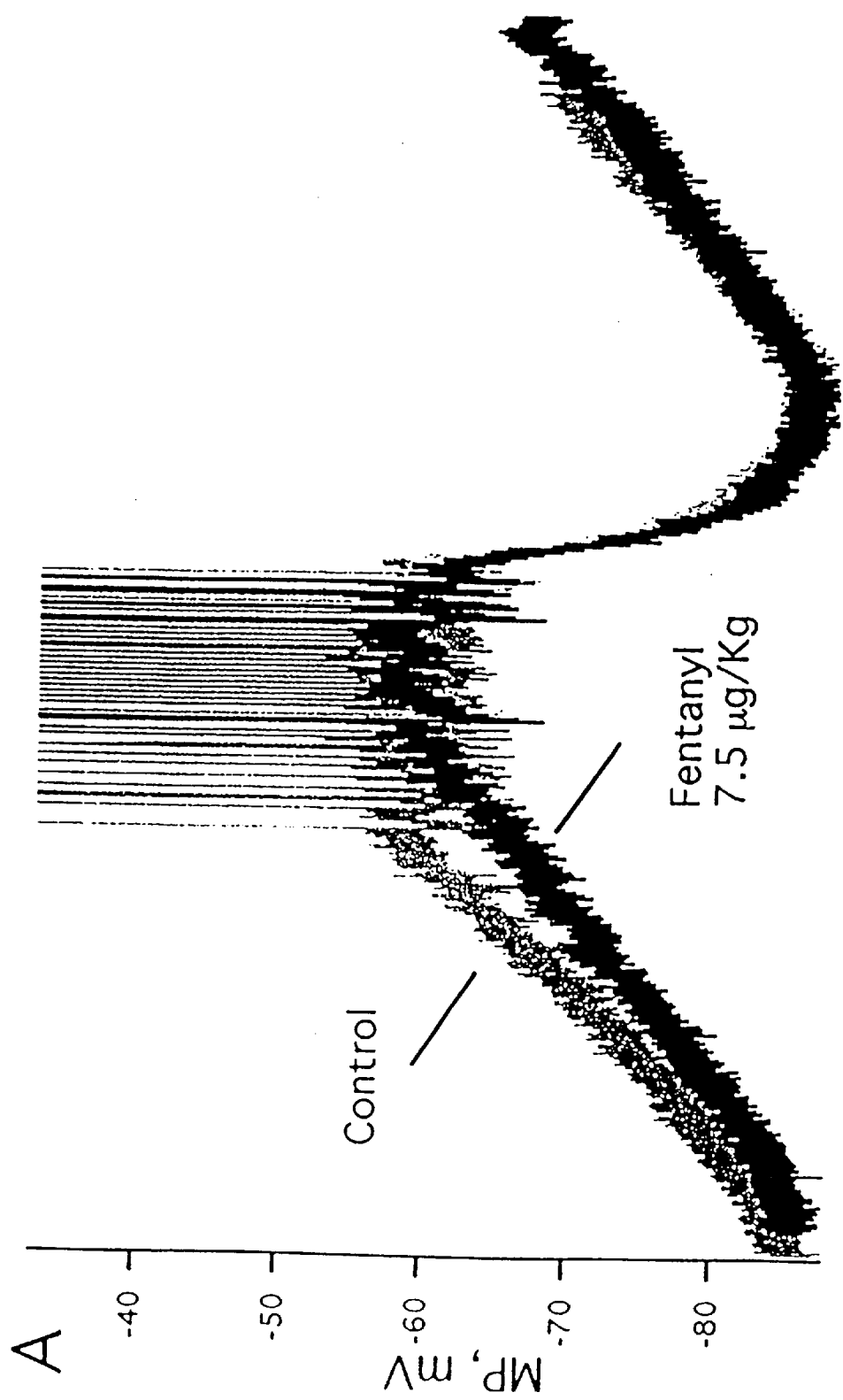
FIGS. 4A, 4B, 4C, and 4D are a series of graphs showing the depressant effects of subapneic intravenous doses of fentanyl, a µ-selective opioid receptor agonist, on an augmenting expiratory (Aug-E) bulbospinal neuron.
Figure 4B:
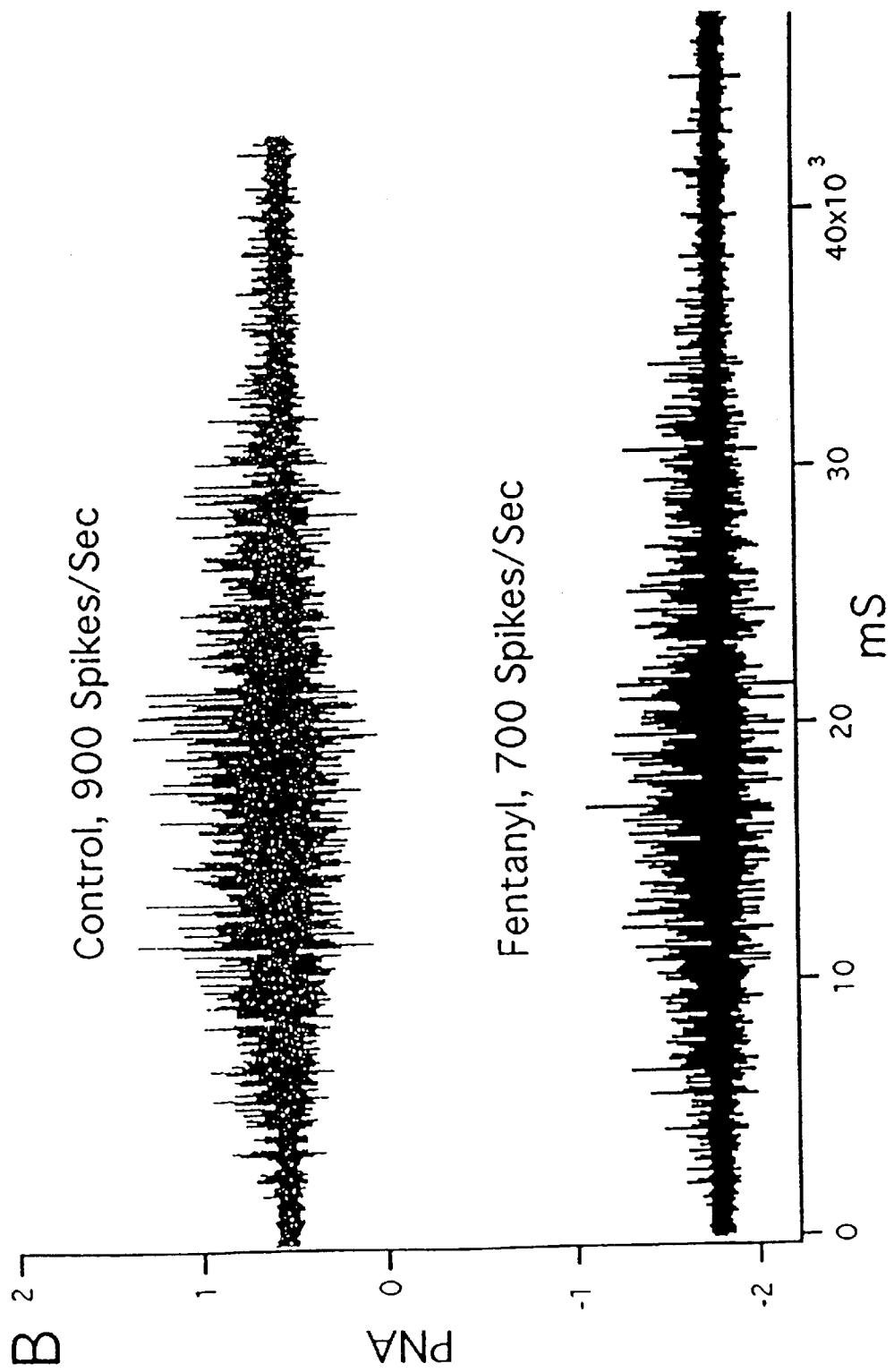

In all effective doses, fentanyl produced depression of neuron excitability that was accompanied by changes in phrenic nerve activity. Lowest doses (5–7.5 μg/kg, n=6 cells) reduced the amplitude and rate of depolarization of excitatory synaptic drive potentials in Aug-E neurons within 30 seconds of administration, in advance of changes in PN activity. The effects on synaptic drive potentials caused Aug-E neurons to discharge more briefly and at lower frequency (FIGS. 4A and 4B). Within 45 seconds, PN discharge intensity was also reduced and the expiratory silent period of PN activity was prolonged.

Figure 4C:
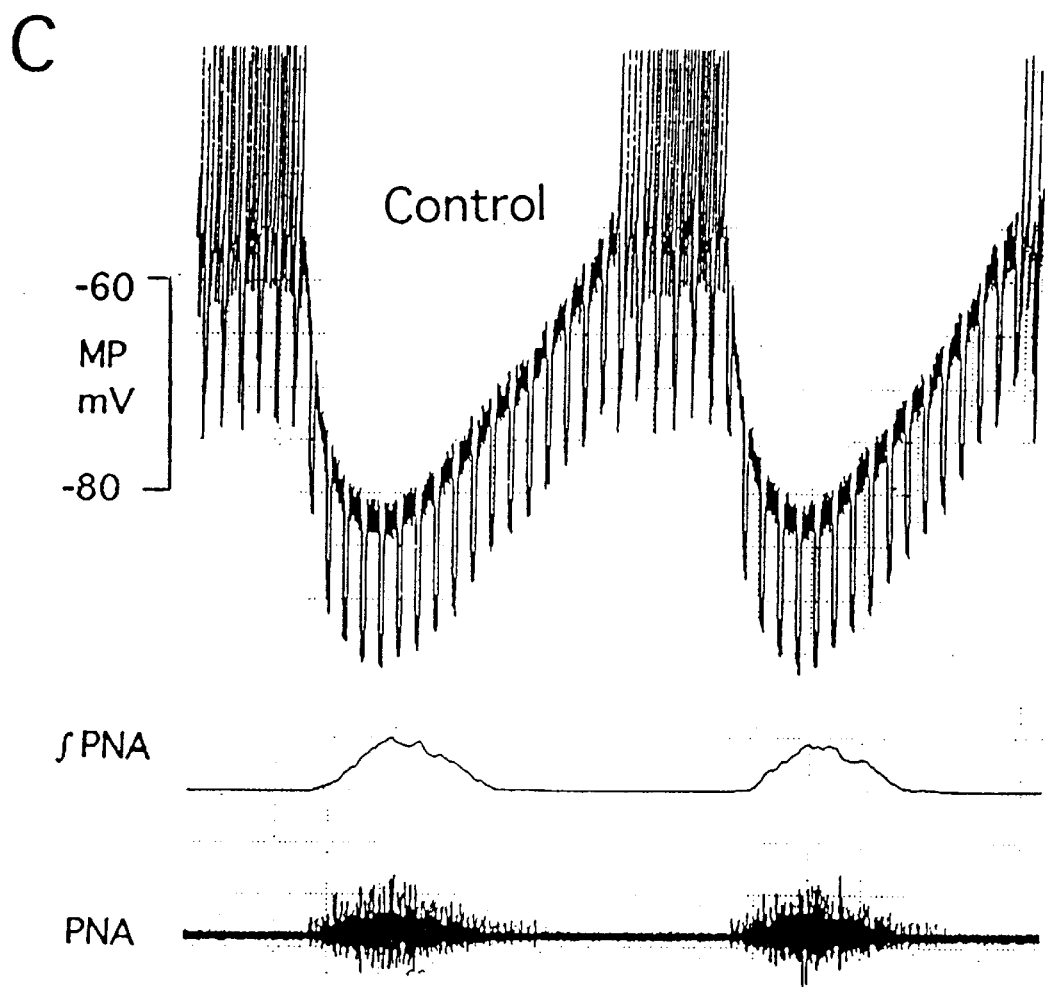
Figure 4D:
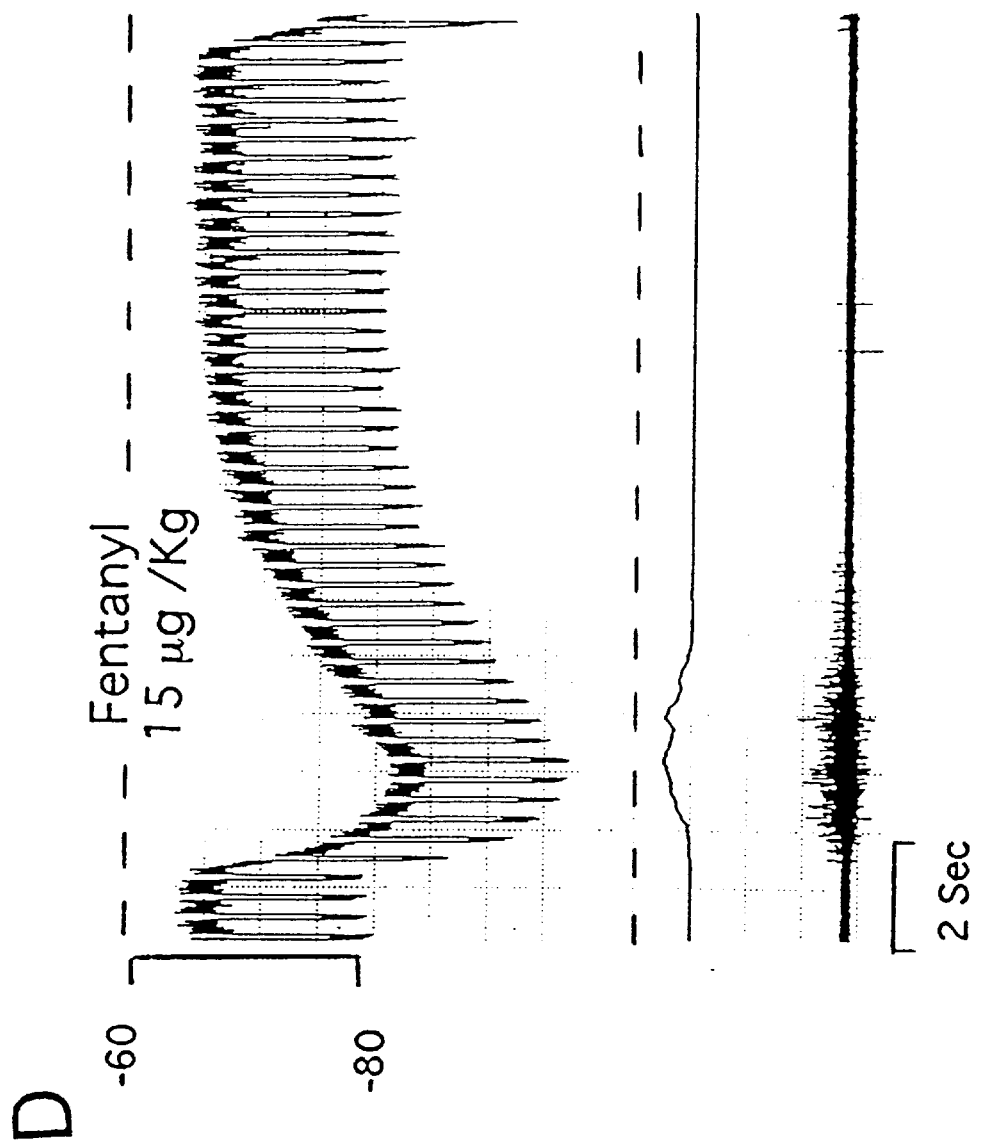

Larger doses (7.5–15 μg/kg) further depressed Aug-E excitatory synaptic drive potentials to below threshold and prolonged their duration (n=14 cells; see FIG. 4C (control) and FIG. 4D). In one cell, inspiratory MP was more hyperpolarized than control after 12 μg/kg (not illustrated). In parallel with the disturbances of Aug-E rhythm and excitability, PN discharge intensity was further reduced and the expiratory phase silent periods were further prolonged.

Figure 5A:
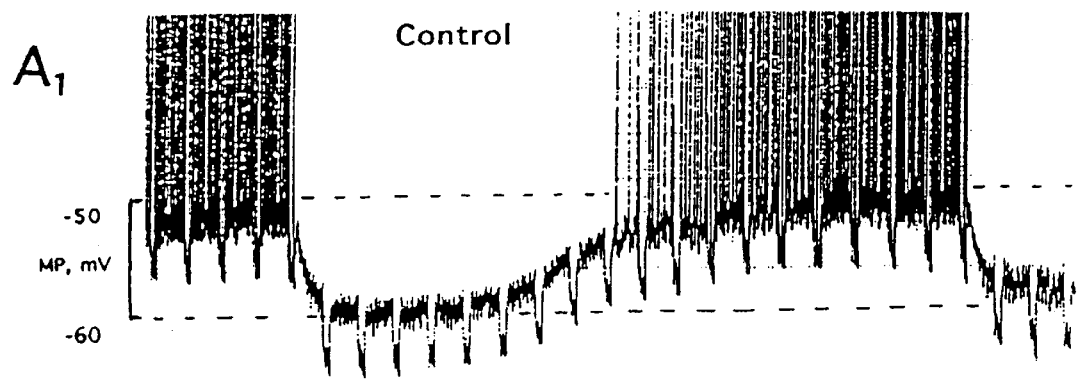
FIGS. 5A, 5B, 5C, and 5D show the effects of doses of fentanyl that severely depress or abolish phrenic nerve activity on membrane properties of bulbospinal Aug-E neurons. Results are from tests on two Aug-E neurons in two-pentobarbital-anesthetized cats (contols shown in FIGS. 5A and 5C, after administration of fentanyl shown in FIGS. 5B and 5D). The figures illustrate membrane potential (mV), phrenic nerve activity (PN) and the moving average of phrenic nerve action potential frequency (PNa). Dashed lines are references denoting control membrane potential. Regularly spaced downward deflections of membrane potential, used to monitor changes of neuron input resistance (Rn), were produced by 60 mS, hyperpolarizing constant current pulses. Note that the effects on membrane potential and discharge properties of Aug-E neurons were accompanied by only small increases of $R_n$.
Figure 5B:
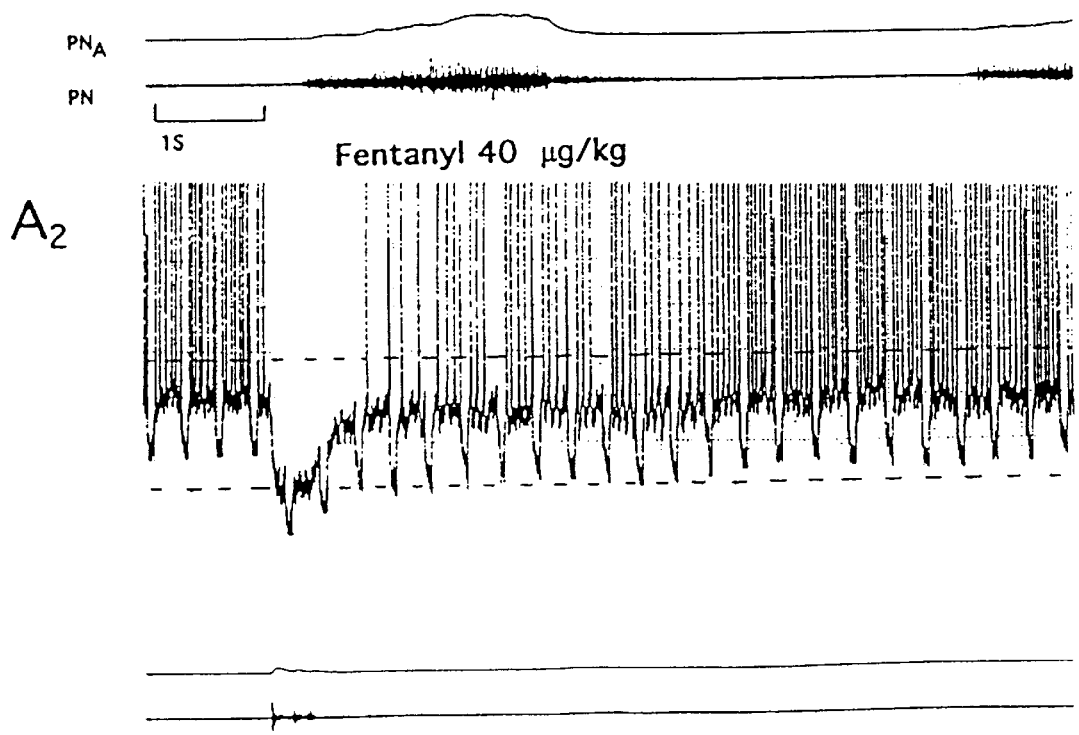

Following doses of fentanyl which eliminated the normal three-phase PN rhythm but permitted brief, sporadic (2–3 per min) bursts of gasp-like PN activity (15–40 μg/kg), membrane potential of Aug-E neurons no longer exhibited rhythmic fluctuations but became steady just above threshold at around −60 mV (n=6). Consequently, a tonic discharge of action potentials was triggered at 12–15 Hz (see FIG. 5A (control) and FIG. 5B), compared to 20–40 Hz observed during the normal expiratory bursts observed under control conditions (FIG. 5A). Tonic firing was terminated briefly by membrane potential hyperpolarization during the gasp-like PN discharges. The effects of fentanyl on membrane potential and discharge properties of Aug-E neurons occurred without significant change of neuron input resistance.

Figure 5C:
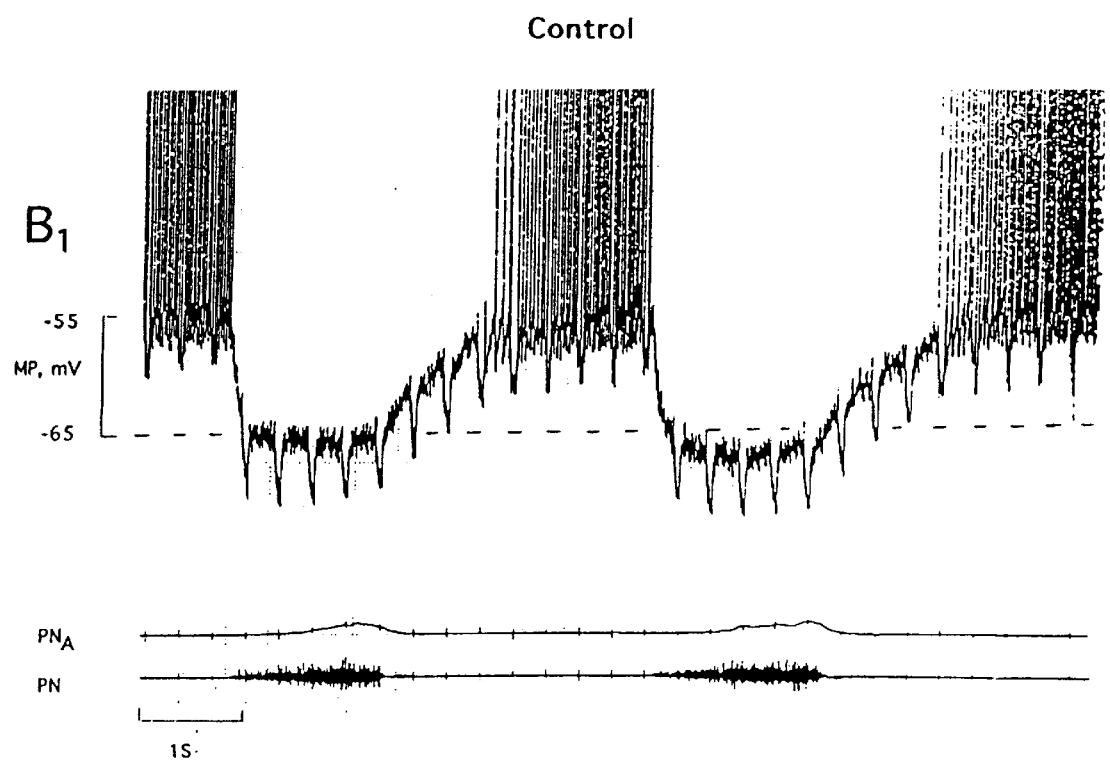
Figure 5D:
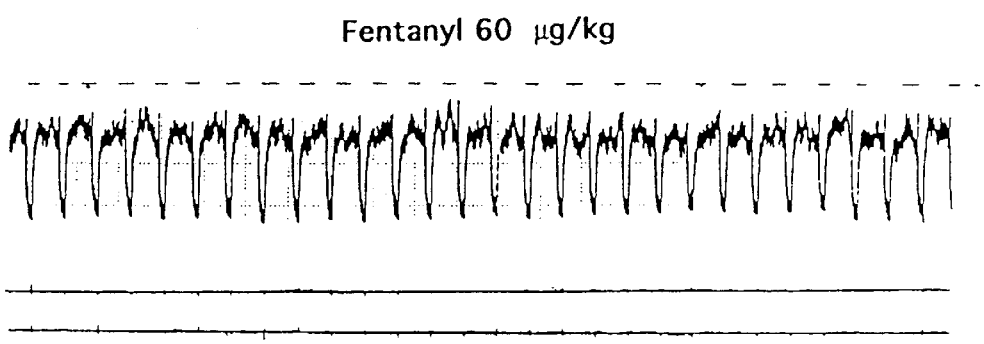

In tests where cumulative doses of fentanyl eliminated all PNA (20–120 μg/kg), including gasp-like discharges, membrane potential of Aug-E neurons (n=4) reached steady levels that ranged from 4 mV (20–60 μg/kg fentanyl) to 20 mV (60–120 μg/kg), values more negative than the threshold for action potential generation (see FIGS. 5C and 5D). A small increase in neuron input resistance (less than 10%) accompanied the membrane potential changes. Recovery of PN activity from apnea to control levels required 45–56 minutes. It was never possible to maintain stable MP conditions in the Aug-E neurons long enough to record spontaneous recovery. However, complete recovery was affected in two Aug-E neurons, along with PNA, after administering systemic naloxonazine (40 μg/kg i.v.) (data not illustrated).

EXAMPLE 4
Effects of Fentanyl on an Aug-E Neuron Properties Recorded During Voltage Clamp Voltage clamp measurements made on two Aug-E neurons revealed additional depressant effects of fentanyl. Under control conditions, alternating waves of outwardly directed current during the inspiratory phase and inwardly directed current during the expiratory period were present, consistent with findings in previous studies (see FIGS. 6A and 7A; see also Richter et al., 1996).

Figure 6A:
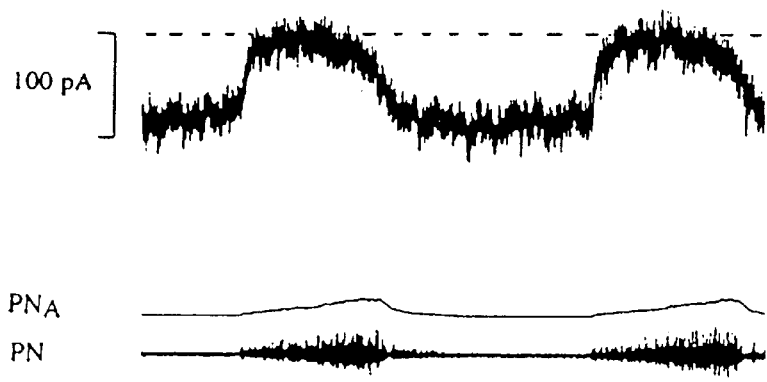
FIGS. 6A through 6F show the effects of fentanyl and hypercapnia on membrane potential and membrane current in an Aug-E neuron. All recordings are from a pentobarbital-anesthetized cat.
Figure 6B:

After giving 100 μg/kg to one cat, PN activity was abolished, membrane potential was hyperpolarized (FIG. 6E), and a persistent outward current developed (FIG. 6B). Fast excitatory postsynaptic potentials (EPSPs) and postsynaptic currents (EPSCs) also occurred during the inspiratory and expiratory phases. Synaptic activity was still occurring because fast EPSCs and EPSPs were still evident although frequencies were reduced. Hypercapnea (52 torr $CO_2$) produced by decreasing the rate of ventilation while maintaining a high level of inspired of oxygen (534 torr) did not restore the respiratory rhythm, but did reduce MP hyperpolarization and outward current and increased fast EPSP and EPSC frequencies.

Figure 6C:
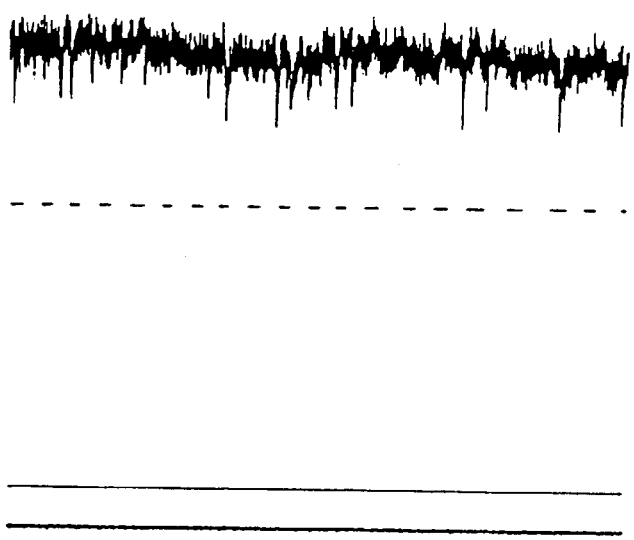
Figure 6D:
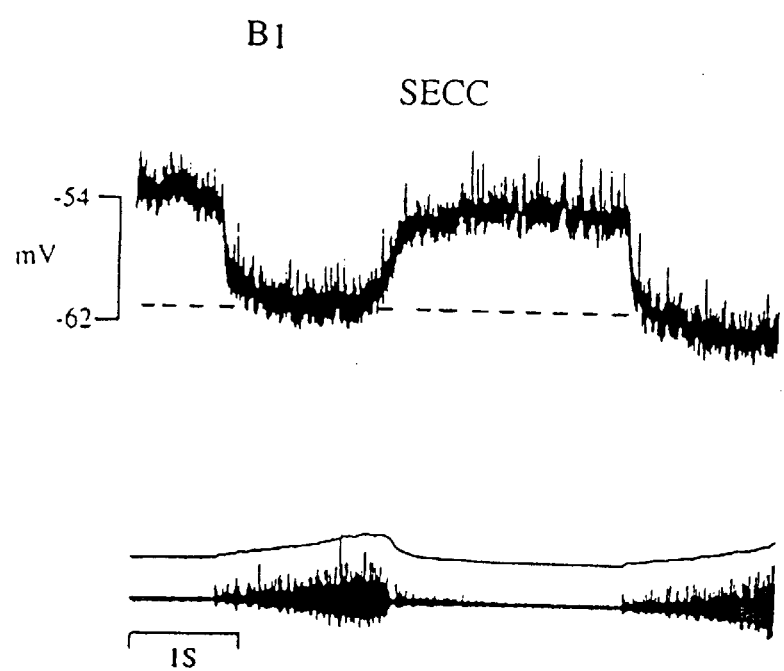
Figure 6E:
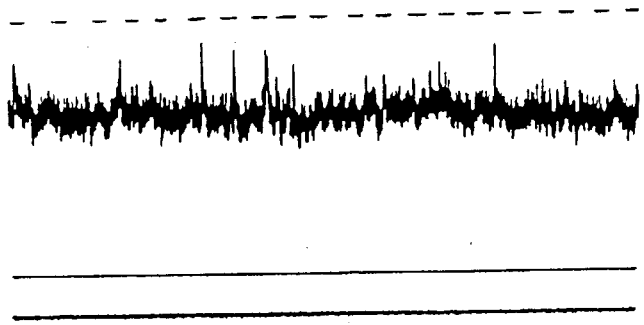
Figure 6F:

FIGS. 6A, 6B, and 6C show membrane currents (pA) in a non-discharging E neuron recorded during single electrode voltage clamp {SEVC, holding potential (HP) −70 mV, 30 KHz switching frequency, 25% duty cycle}. FIGS. 6D, 6E, and 6F show membrane potential (mV) when recording was switched to current clamp (SECC). Records of phrenic nerve activity (PN) and the moving average of phrenic nerve action potential frequency ($PN_A$) are also shown in each figure. Dashed lines denote control levels of inspiratory phase outward current and membrane potential hyperpolarization. Controls are shown in FIGS. 6A and 6D. After administering fentanyl (100 μg/kg i.v.) (FIGS. 6B and 6E), the respiratory rhythm was abolished. Membrane potential was hyperpolarized and an increase in outward current occurred. EPSP and EPSC frequency was reduced but amplitude did not change appreciably. Hypercapnea produced by ventilation with a mixture of 5% $CO_2$, 95% $O_2$ and room air shifted membrane potential and current back toward control levels, but was insufficient to restore the respiratory rhythm (FIGS. 6C and 6F).

Figures 7A, 7B:
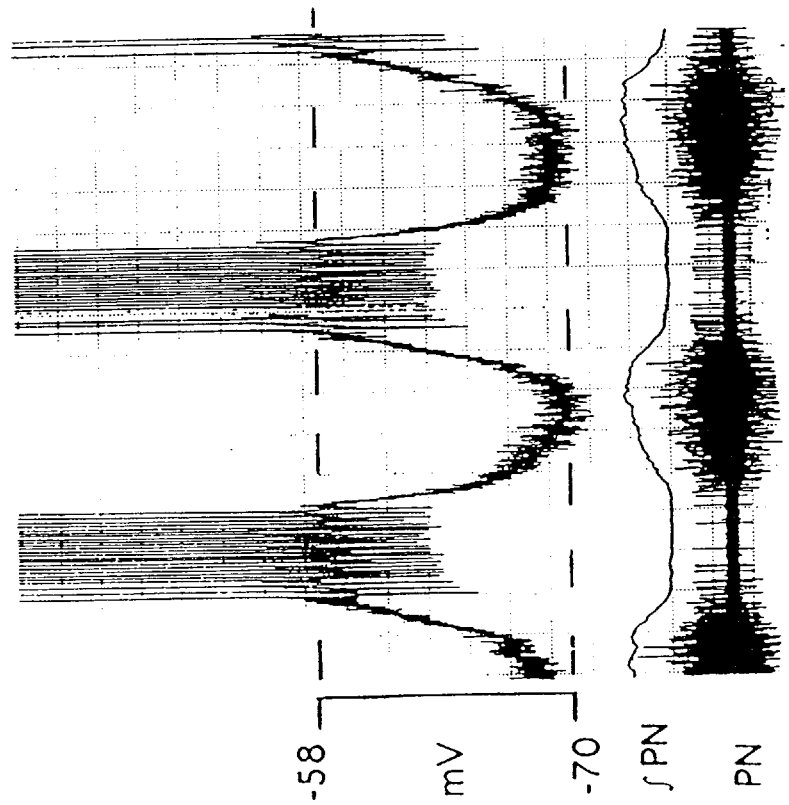
FIGS. 7A through 7F show that the depressant effects of fentanyl on membrane potential and membrane currents of an Aug-E neuron are reversed by carotid body chemorceptor stimulation with doxapram. All figures are in a chloralose-anesthetized cat.
Figures 7C, 7D:
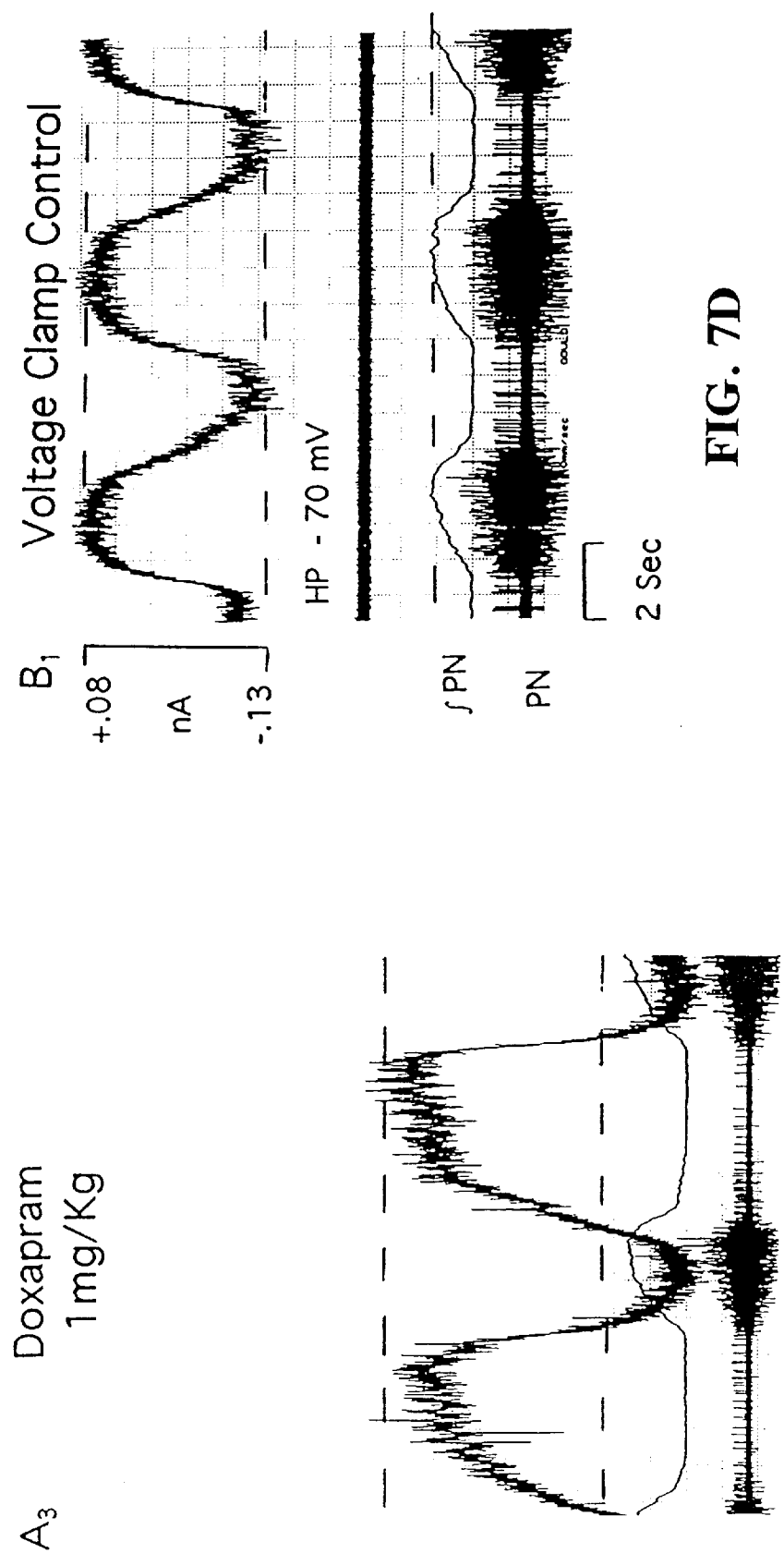
Figure 7F:
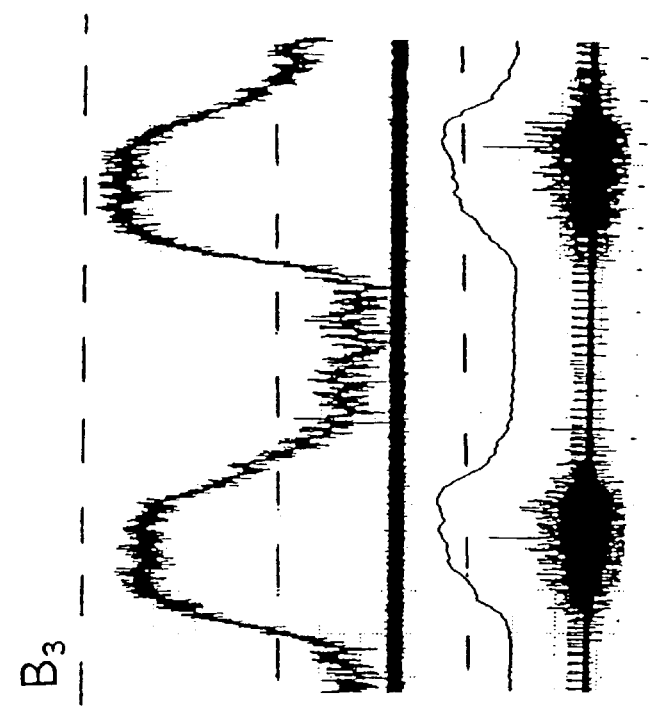
Figure 7E:
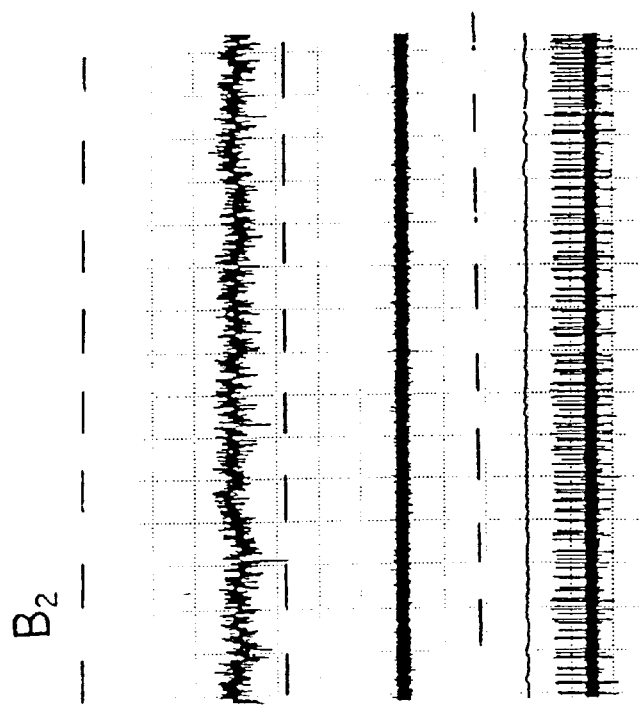

In another Aug-E neuron recorded in a chloralose-anesthetized cat (see FIGS. 7A through 7F), a smaller dose of fentanyl was given that was just sufficient to induce PN apnea (20 μg/kg). Under control conditions, the neuron discharged rhythmically (FIG. 7A). Inward current reached 130 pA during the discharge phase (FIG. 7D). After fentanyl administration, membrane potential was steady at just below threshold (FIG. 7B). A steady inward current of 90 pA current was evident (FIG. 7E), indicating that despite the apnea substantial tonic excitatory synaptic transmission was preserved. Intravenous injection of the carotid body chemoreceptor stimulant doxapram reinstated PN activity as well as synaptic drive potentials and currents.

EXAMPLE 5
Reversal of Opioid-Mediated Respiratory Effects by $D_1$ Dopamine Receptor Agonists In this example, the $D_1$-dopamine receptor agonists (±)-chloro-APB and (±)-SKF-38393; given in doses of 1.5–3.0 mg/kg i.v., consistently restored the three-phase PN respiratory rhythm after fentanyl had disturbed or abolished it. (±)-Chloro-APB was tested in two pentobarbital-anesthetized cats, three chloralose-anesthetized cats, and three decerebrate unanesthetized cats. (±)-SKF-38393 was tested in two decerebrate cats and one chloralose-anesthetized cat.

Figure 8A:
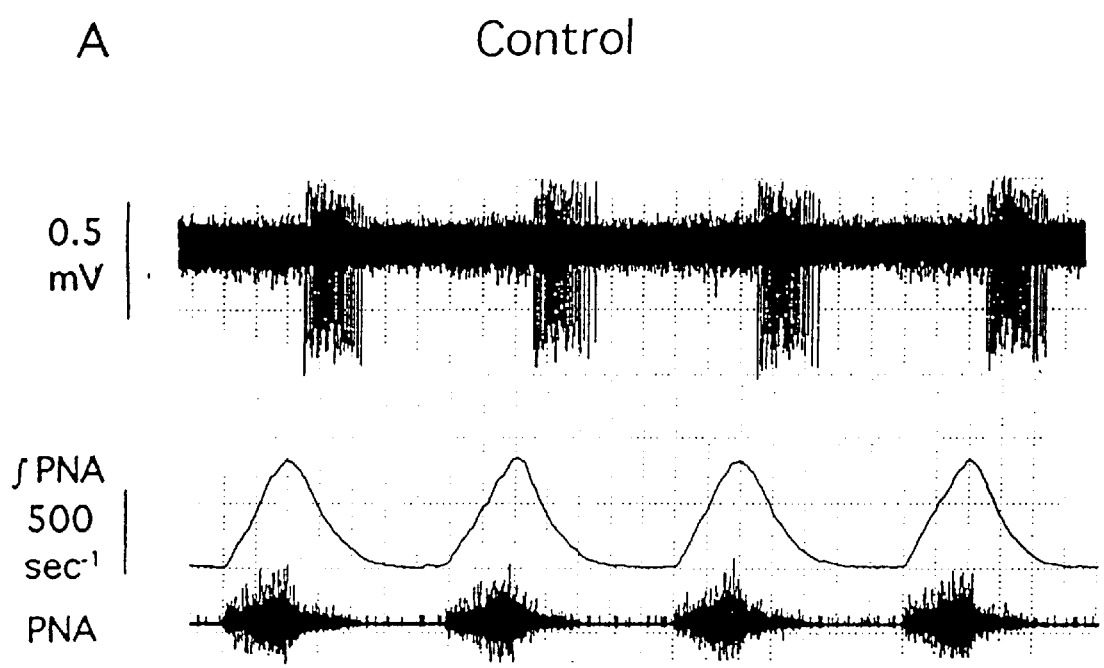
FIGS. 8A, 8B, 8C and 8D are a series of tracings showing the reversal of opioid-mediated depression of the respiratory network by (±)-chloro-APB, a $D_1$-dopamine receptor agonist. In each of FIGS. 8A through 8D, the traces are, from top to bottom in each figure: extracellular records of discharge activity from a non-bulbospinal postinspiratory (PI) neuron, integrated discharges of phrenic nerve (∫PNA), and raw phrenic nerve activity (PNA).
Figure 8B:
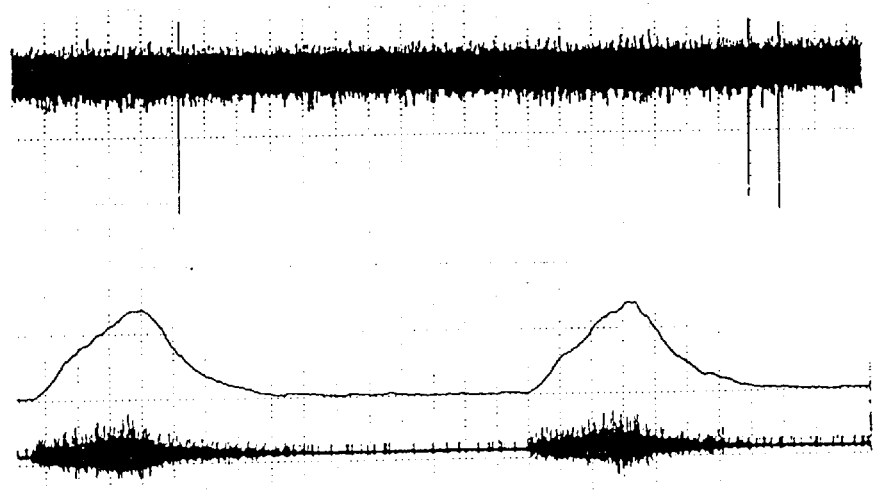
Figure 8C:
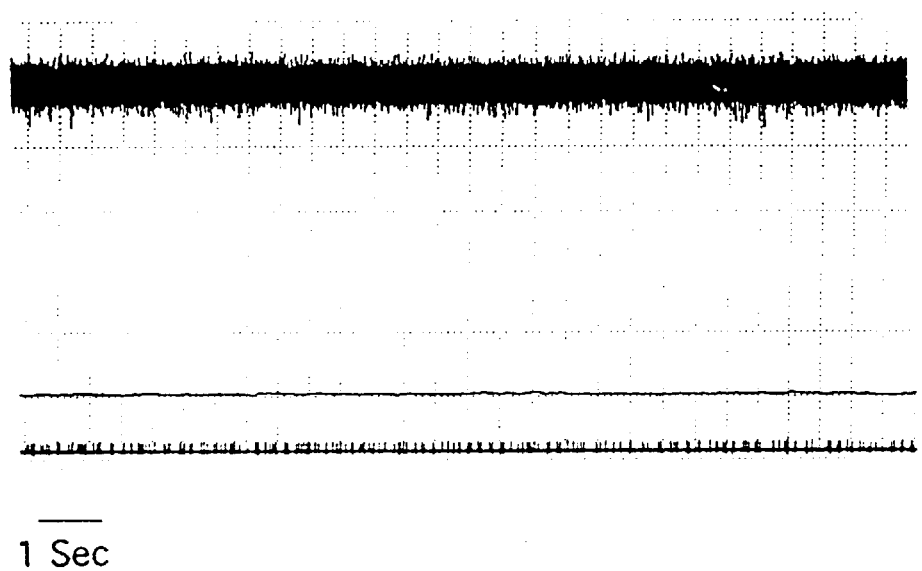
Figure 8D:
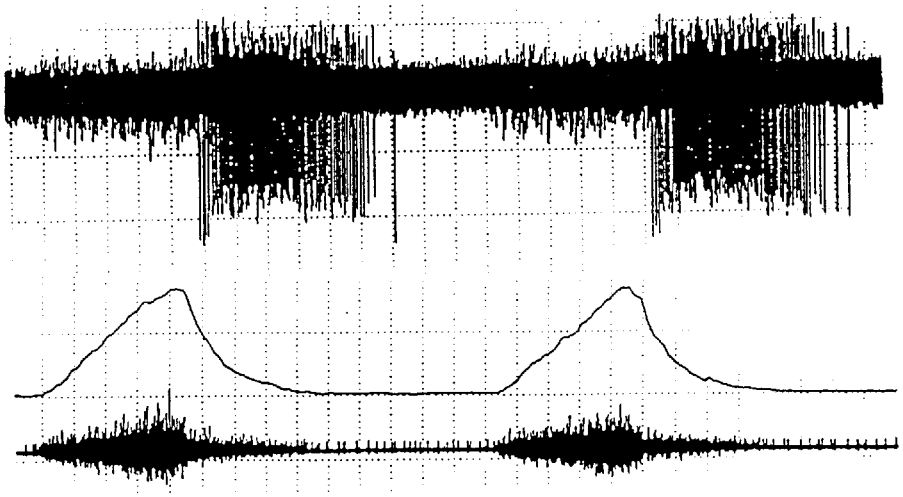

An example of apnea reversal produced in a chloralose-anesthetized cat by (±)-chloro-APB is shown in FIGS. 8A through 8D, which also reveal the high sensitivity of postinspiratory (PI) neurons to depression. FIG. 8A is the control; FIGS. 8B and 8C show the early and late effects of a 30 μg/kg dose of fentanyl, respectively. Over a period of 2 minutes following opioid administration, PN activity was first disturbed and then abolished. The PI neuron discharges were depressed and then abolished ahead of the PNA. Injection of a cumulative dose of 3 mg/kg (±)-chloro-APB restored inspiratory and postinspiratory PN discharges, FIG. 8D. The inspiratory, postinspiratory and expiratory phases of PNA were longer than in the control, resulting in a slower respiratory cycle, and PI neuron discharges were much longer. Increasing the dose to 4.5 mg/kg (±)-chloro-APB produced no further change. Identical effects of (±)-chloro-APB in restoring PNA and firing of a PI neuron after opioid-induced apnea were observed in another chloralose-anesthetized cat. The two PI neurons neurons tested in this study were not activated antidromically by stimulation of the cervical reticulospinal tracts.

Figure 9A:
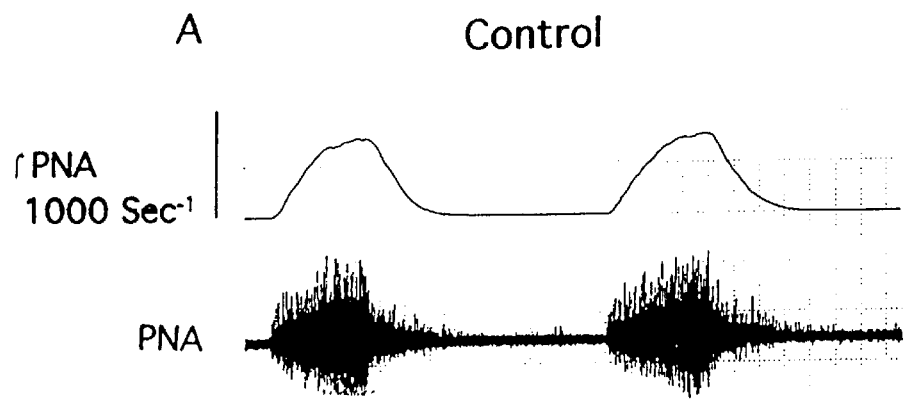
FIGS. 9A through 9F are a series of tracings showing that $D_1$-dopamine receptor blockade prevents reversal of opioid-mediated respiratory neuron depression, but does not prevent restoration of respiratory nerve discharges by carotid body chemoreceptor stimulation. In each of FIGS. 9A through 9F, the top trace records integrated phrenic nerve activity (∫PNA) and the bottom trace records raw phrenic nerve activity (PNA). All tracings recorded in a pentobarbital-anesthetized cat.
Figure 9B:
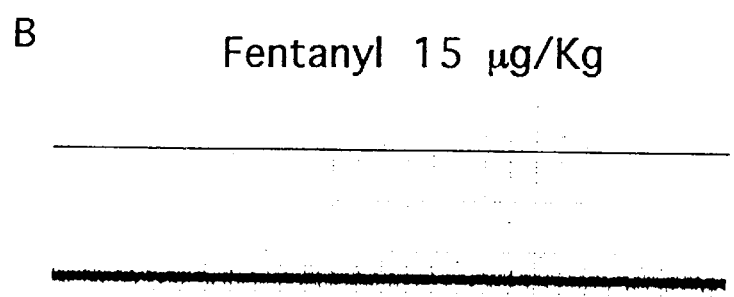
Figure 9C:
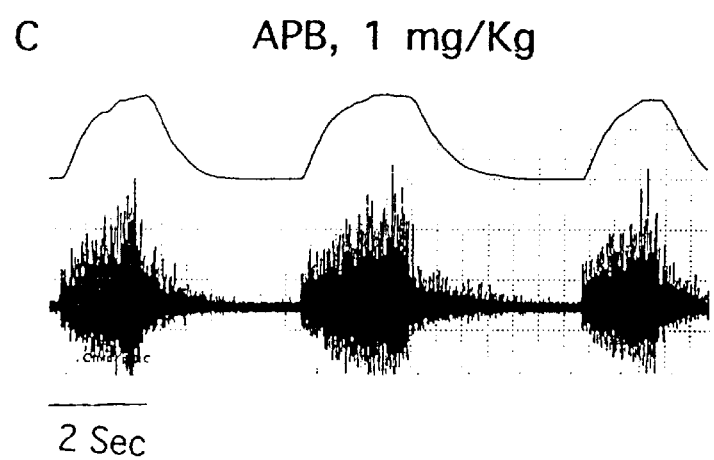

EXAMPLE 6
The Effects of (±)-Chloro-APB and (±)-SKF-38383 on PN Activity are Blocked by a $D_1$ Dopamine Receptor Antagonist To test whether the restoration of PN activity by (±)-chloro-APB or (±)-SKF-38393 was indeed linked to activation of $D_1$-dopamine receptors, three animals (one pentobarbital-anesthetized, one chloralose-anesthetized, one decerebrate) were pretreated with the selective receptor antagonist (R)(+)-SCH-23390 just prior to $D_1$-agonist testing. Results from one test on a pentobarbital-anesthetized cat are shown in FIGS. 9A, 9B, and 9C. FIG. 9A (control), FIG. 9B (after administration of fentanyl), and FIG. 9C (with subsequent administration of (±)-chloro-APB collectively show that (±)-chloro-APB (1 mg/kg) restored PN discharges during apnea produced by fentanyl.

The same dose of fentanyl given one hour later again abolished PN activity, but (±)-chloro-APB (1–3 mg/kg) failed to restore PN discharges after pretreatment with R(+)-SCH-23390. Results were identical in two chloralose-anesthetized cats when (±)-SKF-38393 was preceded by R(+)-SCH-23390, indicating that restoration of PN discharges was linked to agonist actions on $D_1$-dopamine receptors.

Figure 9D:
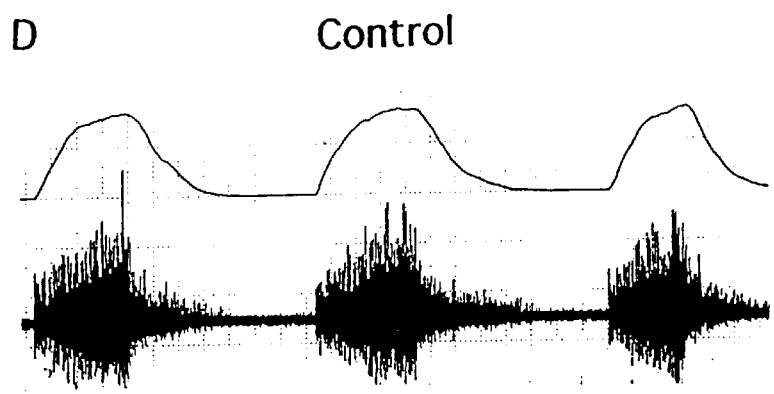
Figure 9E:
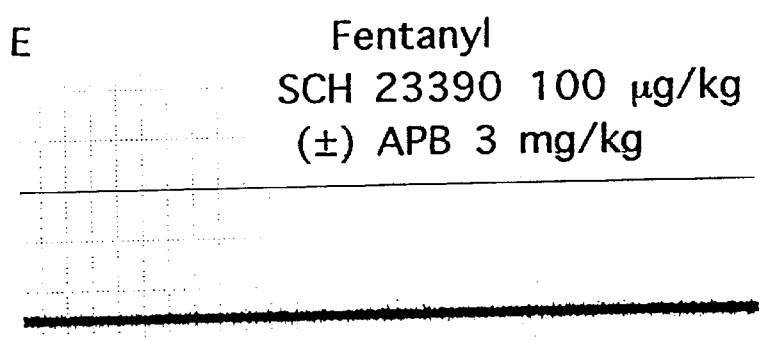
Figure 9F:
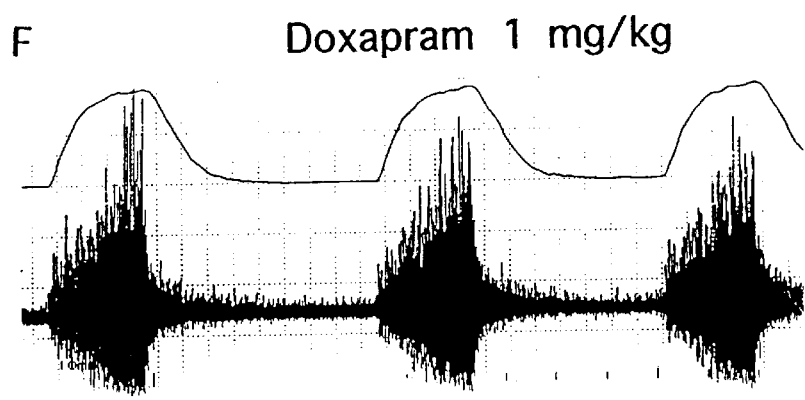

After R(+)-SCH-23390 had blocked $D_1$ agonist effects in the three tests, i.v. injection (0.5–1.0 mg/kg) of the carotid body chemoreceptor stimulant doxapram (Hirsh and Wang, 1974; McCrimmon and Lalley, 1982) evoked strong PN discharges at the same frequency as control; compare FIGS. 9D (control), 9E (after administration of fentanyl, R(+)-SCH-23390 and (±)-chloro-APB) and 9F (with subsequence administration of doxapram). Similar restoration of firing was observed when doxapram was tested during fentanyl-mediated apnea in the absence of $D_1$ agonists and antagonists. It must therefore be assumed that the ability of $D_1$ agonists to reinstate respiratory discharges does not involve agonist occupation of $D_1$ receptors on carotid body chemoreceptor cells.

EXAMPLE 7

Effects of Fentanyl and $D_1$ Dopamine Receptor Agonists on the $CO_2$ Sensitivity of the Respiratory Network Because opioid-mediated depression of ventilation in humans is associated with blunting of the respiratory network's sensitivity to $CO_2$ (Shook et al, 1990), the possibility that $D_1$ agonists reinstate respiratory discharges by increasing $CO_2$ sensitivity was tested. Peak integrated phrenic nerve activity is reported to be an accurate index of tidal volume (Eldridge, 1971). This parameter was used to evaluate the effects of fentanyl and (±)-chloro-APB on the $CO_2$ responsiveness of the respiratory neural network. Tests with fentanyl were made on one pentobarbital-anesthetized cat and with (±)-chloro-APB on six cats (one unanesthetized decerebrate, one pentobarbital-anesthetized, four chloralose-anesthetized). In all experiments, inspired oxygen was maintained at 500–570 torr, so that hemoglobin was oxygen-saturated throughout the tests. End tidal $CO_2$ ($ETCO_2$) was varied between 20–60 Torr by changing the rate of ventilation. Ventilation rates were varied three times under control conditions and three times during each drug test. Measurements of PN activity were made at identical values of $ETCO_2$.

Figure 10:
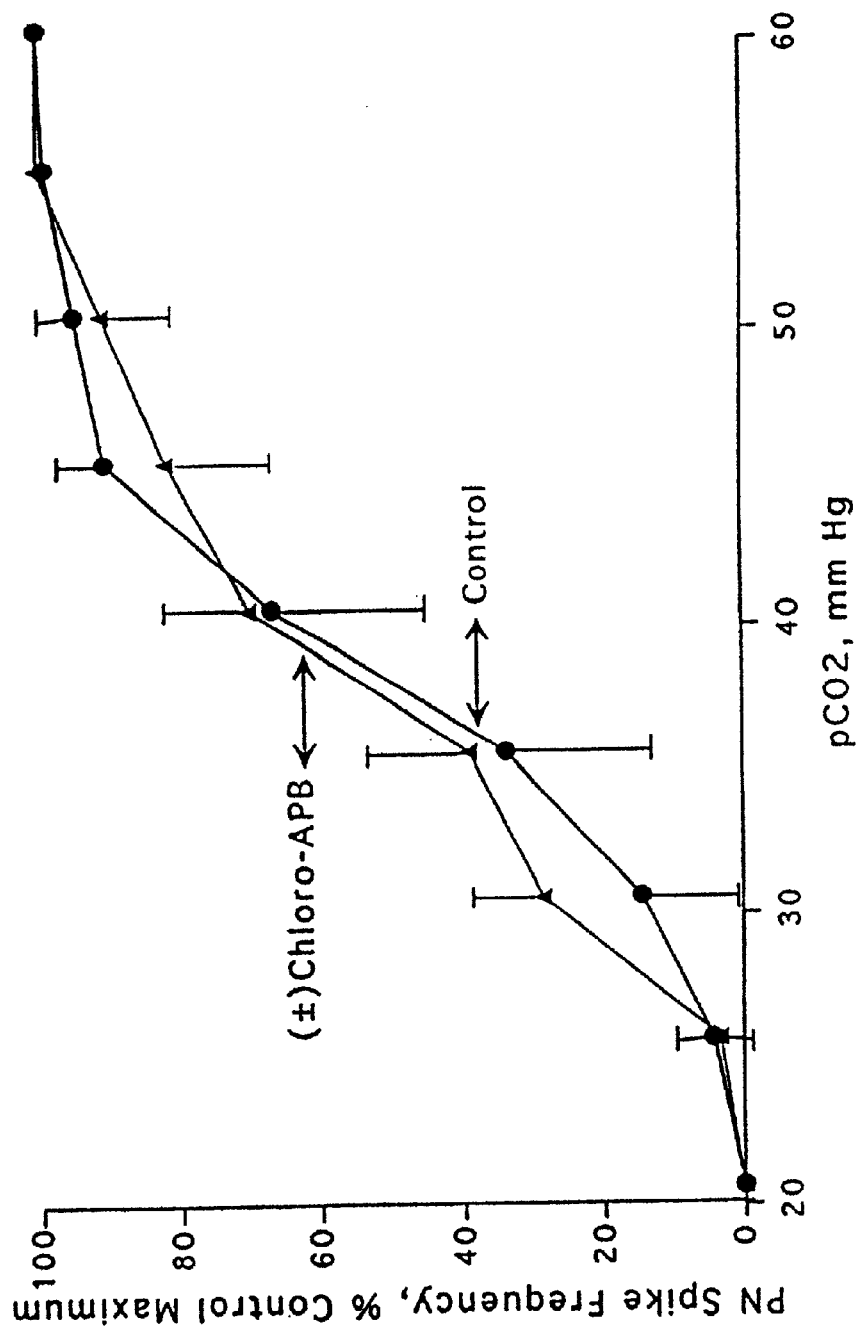
FIG. 10 is a graph showing the effects of systemically administering (±)-chloro-APB (triangles) on the $CO_2$ sensitivity of the respiratory neural network. This figure illustrates that the restoration of breathing by $D_1$-dopamine receptor agonist is not due to an increase in respiratory sensitivity to $CO_2$. The Y-axis plots the peak integrated spike frequency recorded from phrenic nerves during the inspiratory phases; the X-axis plots values of end-tidal $pCO_2$ obtained by varying ventilatory rate. At each level of $pCO_2$ under control conditions and after drug administration, ten measurements of peak integrated spike frequency were made and an average at each level of $pCO_2$ was calculated and converted to percent control. Three runs were performed before and three runs performed after each drug treatment in which $pCO_2$ was brought to the levels represented on the X-axis. Data for the (±)-chloro-APB trace were obtained by pooling results from one chloralose-anesthetized cat, one pentobarbital-anesthetized cat, and one unanesthetized decerebrate cat.

As expected, fentanyl blunted the $CO_2$ responsiveness of phrenic nerve activity. After giving fentanyl (10–15 µg/kg), apnea occurred at higher levels of $ETCO_2$, and higher levels of $CO_2$ were required to affect peak PN spike frequencies that were comparable to control values (data not shown). (±)-Chloro-APB (3 mg/kg), however, did not significantly alter the sensitivity of PN activity to $CO_2$ (see FIG. 10). Thus, the reversal of opioid-mediated respiratory depression by $D_1$ agonists apparently cannot be attributed to an increased respiratory sensitivity to $CO_2$. Further evidence against this mechanism was that the $D_1$ agonists alone did not change PN activity (n=6 cats, data not illustrated).

What is claimed is:

1. A method of eliminating or inhibiting respiratory depression in mammals during treatment with opiates or opioids, the method comprising: administering to a mammalian subject being treated with opiates or opioids an amount of a $D_1$-dopamine receptor agonist that is not (±)-6-chloro-7,8-dihydroxy-3-allyl-1-phenyl-2,3,4,5-tetrahydro-1H-3-benzazepine, the amount being sufficient to inhibit respiratory depression.

2. The method of claim 1, wherein the mammalian subject is a human.

3. The method of claim 1, wherein the $D_1$-dopamine receptor agonist is administered systemically.

4. The method of claim 3, wherein the $D_1$-dopamine receptor agonist is administered intravenously.

5. The method of claim 1, wherein the $D_1$-dopamine receptor agonist is administered to the subject in an amount ranging from about 0.01 to about 50 mg/kg body weight per day.

6. The method of claim 1, wherein the $D_1$-dopamine receptor agonist is administered to the subject in an amount ranging from about 0.1 to about 10 mg/kg body weight per day.

7. A method of eliminating or inhibiting respiratory depression in mammals during treatment with opiates or opioids, the method comprising: administering to a mammalian subject being treated with opiates or opioids, an amount of a $D_1$-dopamine receptor agonist, the amount being sufficient to inhibit respiratory depression, and wherein the $D_1$-dopamine receptor agonist is selected from the group consisting of:
   (±)-1-phenyl-2,3,4,5-tetrahydro-(1H)-3-benzazepine-7,8-diol;
   (−)-(6aR,12bR)-4,6,6a,7,8,12b-hexahydro-7-methylindolo{4,3-a}phenanthridine;
   (±)-trans-10,11-dihydroxy-5,6,6a,7,8,12b-hexahydrobenzo{a}phenanthridine;
   (±)-6-chloro-7,8-dihydroxy-1-phenyl-2,3,4,5-tetrahydro-1H-3-benzazepine;
   (−)-trans-9,10-diacetyloxy-2-propyl-4,5,5a,6,7,11b-hexahydro-3-thia-5-azacyclopent-1-ena[c]phenanthrene hydrochloride enriched or pure enantiomers or diastereomers thereof; racemic mixtures thereof; and pharmaceutically-suitable salts thereof.

8. The method of claim 7, wherein the mammalian subject is a human.

9. The method of claim 8, wherein (±)-1-phenyl-2,3,4,5-tetrahydro-(1H)-3-benzazepine-7,8-diol is administered to the subject.

10. The method of claim 8, wherein (−)-(6aR,12bR)-4,6,6a,7,8,12b-hexahydro-7-methylindolo{4,3-a}phenanthridine is administered to the subject.

11. The method of claim 8, wherein (±)-trans-10,11-dihydroxy-5,6,6a,7,8,12b-hexahydrobenzo-{a}phenanthridine is administered to the subject.

12. The method of claim 8, wherein (±)-6-chloro-7,8-dihydroxy-1-phenyl-2,3,4,5-tetrahydro-1H-3-benzazepine is administered to the subject.

13. The method of claim 8, wherein (−)-trans-9,10-diacetyloxy-2-propyl-4,5,5a,6,7,11b-hexahydro-3-thia-5-azacyclopent-1-ena[c]phenanthrene hydrochloride is administered to the subject.

14. The method of claim 7, wherein the $D_1$-dopamine receptor agonist is administered systemically.

15. The method of claim 14, wherein the $D_1$-dopamine receptor agonist is administered intravenously.

16. The method of claim 7, wherein the $D_1$-dopamine receptor agonist is administered to the subject in an amount ranging from about 0.01 to about 50 mg/kg body weight per day.

17. The method of claim 7, wherein the $D_1$-dopamine receptor agonist is administered to the subject in an amount ranging from about 0.1 to about 10 mg/kg body weight per day.

18. A pharmaceutical composition for inducing analgesia or anesthesia in a mammalian subject, while simultaneously inhibiting respiratory depression in the subject, the composition comprising, in combination, an opiate or opioid analgesic or anesthetic, a $D_1$-dopamine receptor agonist, and a pharmaceutically-suitable carrier therefor, wherein the $D_1$-dopamine receptor agonist is selected from the group consisting of (±)-trans-10,11-dihydroxy-5,6,6a,7,8,12b-hexahydrobenzo{a}phenanthridine;

(±)-6-chloro-7,8-dihydroxy-1-phenyl-2,3,4,5-tetrahydro-1H-3-benzazepine;

(±)-1-phenyl-2,3,4,5-tetrahydro-(1H,-3-benzazepine-7,8-diol;

(−)-trans-9,10-diacetyloxy-2-propyl-4,5,5a,6,7,11b-hexahydro-3-thia-5-azacyclopent-1-ena[c]phenanthrene hydrochloride; enriched or pure enantiomers or diastereomers thereof; racemic mixtures thereof; and pharmaceutically-suitable salts thereof.

19. The pharmaceutical composition of claim 18, wherein the opiate or opioid is selected from the group consisting of alfentanil, buprenorphine, carfentanil, codeine, dihydrocodeine, diprenorphine, etorphine, fentanyl, heroin, hydrocodone, hydromorphone, LAAM, levorphanol, meperidine, methadone, morphine, naloxone, naltrexone, beta-hydroxy-3-methylfentanyl, oxycodone, oxymorphone, propoxyphene, remifentanil, sufentanil, tilidine, tramadol, enriched or pure enantiomers or diastereomers thereof, racemic mixtures thereof, and pharmaceutically-suitable salts thereof.

20. The pharmaceutical composition of claim 18, wherein the $D_1$-dopamine receptor agonist is (±)-1-phenyl-2,3,4,5-tetrahydro-(1H)-3-benzazepine-7,8-diol.

21. The pharmaceutical composition of claim 18, wherein the $D_1$-dopamine receptor agonist is (±)-trans-10,11-dihydroxy-5,6,6a,7,8,12b-hexahydrobenzo{a}phenanthridine.

22. The pharmaceutical composition of claim 18, wherein the $D_1$-dopamine receptor agonist is (±)-6-chloro-7,8-dihydroxy-1-phenyl-2,3,4,5-tetrahydro-1H-3-benzazepine.

23. The pharmaceutical composition of claim 18, wherein the $D_1$-dopamine receptor agonist is (−)-trans-9,10-diacetyloxy-2-propyl-4,5,5a,6,7,11b-hexahydro-3-thia-5-azacyclopent-1-ena[c]phenanthrene hydrochloride.

* * * * *